United States Patent
Goldfinger et al.

(10) Patent No.: US 8,388,860 B2
(45) Date of Patent: *Mar. 5, 2013

(54) CHIRAL COMPOUNDS, LIQUID CRYSTAL COMPOSITIONS AND POLYMER NETWORKS DERIVED THEREFROM

(75) Inventors: Marc B Goldfinger, West Chester, PA (US); Kai Qi, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 11 days.

This patent is subject to a terminal disclaimer.

(21) Appl. No.: 12/672,734

(22) PCT Filed: Aug. 14, 2008

(86) PCT No.: PCT/US2008/073111
§ 371 (c)(1),
(2), (4) Date: Feb. 9, 2010

(87) PCT Pub. No.: WO2009/023759
PCT Pub. Date: Feb. 19, 2009

(65) Prior Publication Data
US 2011/0042614 A1    Feb. 24, 2011

Related U.S. Application Data

(60) Provisional application No. 60/955,934, filed on Aug. 15, 2007.

(51) Int. Cl.
```
C09K 19/34      (2006.01)
C09K 19/52      (2006.01)
C09K 19/06      (2006.01)
C09K 19/00      (2006.01)
C09K 19/02      (2006.01)
```

(52) U.S. Cl. ........... 252/299.61; 252/299.01; 252/299.6; 252/299.66; 252/299.62; 252/299.63; 252/299.64; 252/299.65; 428/1.1; 428/1.2; 349/1; 349/182; 549/464; 526/268

(58) Field of Classification Search ............. 252/299.01, 252/299.61–299.66; 428/1.1, 1.2; 430/20; 549/464; 526/268; 349/1, 182
See application file for complete search history.

(56) References Cited

U.S. PATENT DOCUMENTS

| | | | |
|---|---|---|---|
| 4,637,896 A | 1/1987 | Shannon | |
| 5,788,880 A | 8/1998 | Schierlinger et al. | |
| 5,833,880 A | 11/1998 | Siemensmeyer et al. | |
| 6,010,643 A | 1/2000 | Coates et al. | |
| 6,410,130 B1 | 6/2002 | Schuhmacher et al. | |
| 6,468,444 B1 | 10/2002 | Meyer et al. | |
| 6,723,395 B2 | 4/2004 | May et al. | |
| 6,887,455 B2 | 5/2005 | Carpenter et al. | |
| 7,879,256 B2 * | 2/2011 | Goldfinger et al. | 252/299.67 |
| 7,914,700 B2 * | 3/2011 | Goldfinger et al. | 252/299.01 |
| 2003/0026922 A1 | 2/2003 | May et al. | |

FOREIGN PATENT DOCUMENTS

| | | |
|---|---|---|
| DE | 4408170 | 9/1995 |
| EP | 261712 | 3/1988 |
| EP | 331233 | 9/1989 |
| EP | 397263 | 11/1990 |
| JP | 2005/004389 | 10/2003 |
| WO | 1998047979 | 10/1998 |
| WO | 2006/128091 | 11/2006 |

OTHER PUBLICATIONS

Bassler et al., Helical Twisting Power of Steroidal Solutes in Cholesteric Mesophases, J. Chem Phys., 1970, vol. 52, pp. 631-637.
Strohriegl et al., Photopolymerizable Cholesteric Liquid Crystals New Materials for Holographic Applications, Advanced Materials, 2000, vol. 12, pp. 1698-1700.
Kurihara et al., Preparation of Helical Polyelectrolyte Networks by Polymerization of Hydrogen Bonding Liquid Crystalline Monomers, Macromolecules, 1998, vol. 31, pp. 5940-5942.
Broer et al., In-Situ Photopolymerization of Oriented Liquid-Crystalline Acrylates 3a, Makromol. Chem., 1989, 190, pp. 2255-2268.
Broer et al., In-Situ Photopolymerization of Oriented Liquid-Crystalline Acrylates 5a, 1991, 192, pp. 59-74.
Hsu et al., Preparation of Liquid-Crystal Thermosets: In Situ Photopolymerization of Oriented Liquid—Crystal Diacrylates, Journal of Polymer Science Part A, 1999, vol. 37, pp. 3929-3935.
Broer et al., In-Situ Photopolymerization of Oriented Liquid Crystalline Acrylates 4a, Makromol. Chem., 1989, vol. 190, pp. 3201-3215.

* cited by examiner

*Primary Examiner* — Geraldina Visconti
(74) *Attorney, Agent, or Firm* — Kevin S. Dobson

(57) ABSTRACT

Isomannide-based compounds having chiral properties are provided, in addition to liquid crystal compositions and polymer networks derived therefrom.

20 Claims, No Drawings

CHIRAL COMPOUNDS, LIQUID CRYSTAL COMPOSITIONS AND POLYMER NETWORKS DERIVED THEREFROM

This application claims the benefit of U.S. Provisional Application No. 60/955,934, filed Aug. 15, 2007, which is by this reference incorporated in its entirety as a part hereof for all purposes.

TECHNICAL FIELD

This invention is related to the chemical synthesis of chiral monomers, liquid crystal compositions comprising the chiral monomers, and polymerization of the liquid crystal compositions to provide polymer networks with useful cholesteric optical properties.

BACKGROUND

Thermotropic liquid crystals are generally crystalline compounds with significant anisotropy in shape. That is, at the molecular level, they are characterized by a rod-like or disc like structure. When heated they typically melt in a stepwise manner, exhibiting one or more thermal transitions from a crystal to a final isotropic phase. The intermediate phases, known as mesophases, can include several types of smectic phases wherein the molecules are generally confined to layers; and a nematic phase wherein the molecules are aligned parallel to one another with no long range positional order. The liquid crystal phase can be achieved in a heating cycle, or can be arrived at in cooling from an isotropic phase. A comprehensive description of the structure of liquid crystals in general, and twisted nematic liquid crystals in particular, is given in "The Physics of Liquid Crystals," P. G. de Gennes and J. Prost, Oxford University Press, 1995.

An important variant of the nematic phase is one wherein a chiral moiety is present therein, referred to as a twisted nematic, chiral nematic, or cholesteric phase. In this case, the molecules are parallel to each other as in the nematic phase, but the director of molecules (the average direction of the rodlike molecules) changes direction through the thickness of a layer to provide a helical packing of the nematic molecules. The pitch of the helix is perpendicular to the long axes of the molecules. This helical packing of anisotropic molecules leads to important and characteristic optical properties of twisted nematic phases including circular dichroism, a high degree of rotary power; and the selective reflection of light, including ultraviolet, visible, and near-IR light. Reflection in the visible region leads to brilliantly colored layers. The sense of the helix can either be right-handed or left-handed, and the rotational sense is an important characteristic of the material. The chiral moiety either may be present in the liquid crystalline molecule itself, for instance, as in a cholesteryl ester, or can be added to the nematic phase as a dopant, leading to induction of the cholesteric phase. This phenomenon is well documented, as discussed for example in H. Bassler and M. M. Labes, J. Chem. Phys., 52, 631 (1970).

There has been significant effort invested in methods for preparing, by synthesis, polymerization and otherwise, stable polymer layers exhibiting fixed cholesteric optical properties. One approach has been to synthesize monofunctional and/or polyfunctional reactive monomers that exhibit a cholesteric phase upon melting, formulate a low melting liquid crystal composition, and polymerize the liquid crystal composition in its cholesteric phase to provide a polymer network exhibiting stable optical properties of the cholesteric phase. Use of cholesteric monomers alone, as disclosed in U.S. Pat. No. 4,637,896, provided cholesteric layers with the desired optical properties, but the polymer layers possessed relatively weak mechanical properties.

Many efforts have been made to improve the physical properties and thermal stabilities by formulating twisted nematic monomer phases that are capable of crosslinking polymerizations to provide polymer networks. A need remains, however, for polymerizable chiral monomers that have good phase compatibility in polymerizable nematic liquid crystals and high helical twisting power (HTP). High HTP allows the use of smaller amounts of the expensive chiral component to be used in twisted nematic formulations to induce a desired pitch. Good phase compatibility is required to prevent premature crystallization or phase separation of the chiral monomers from the twisted nematic formulation. Crosslinking chiral monomers with high HTP and good phase compatibility, based on the isosorbide chiral group, are disclosed in U.S. Pat. No. 6,723,395. However, the chiral monomers based on the isosorbide moiety generally reflect right-handed circular polarized light (RHCPL), as described inter alia.

For many optical applications, both cholesteric twist senses are required, that is a twisted nematic phase that reflects RHCPL and a twisted nematic phase that reflects left-hand circularly polarized light (LHCPL). Despite the disclosures of U.S. Pat. No. 6,468,444 concerning polymerizable chiral compounds based on isosorbitol, isomannitol and iditol, and their uses as chiral dopants for producing cholesteric liquid crystal compositions, a need remains for cholesteric liquid crystal compositions that reflect LHCPL, and particularly for optical films derived from two twisted nematic phases, with opposite twist sense, that can be combined to give nominally 100% reflection of light within a specific reflection band. Thus, needed are chiral monomers that have good phase compatibility with polymerizable nematic phases, exhibit high HTP, and have the ability to induce a twisted nematic phase that reflect LHCPL. There also is a need for polymer networks derived from these chiral monomers that exhibit cholesteric optical properties and reflect LHCPL.

SUMMARY

One embodiment of the inventions disclosed herein is a compound as represented by the structure of the following formula (I):

$$R(S_5A_1)_r(S_3B_1)_pS_1\text{-}D\text{-}S_2(B_2S_4)_q(A_2S_6)_rR_p \qquad (I)$$

wherein

D is the divalent moiety derived from isomannide:

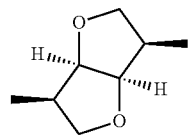

$S_1$ and $S_2$ are linking groups each independently selected from the group consisting of —O—, —OC(O)—, and —OC(O)O—;

$S_3$, $S_4$, $S_5$, and $S_6$, are linking groups each independently selected from the group consisting of covalent bond, —O—, —S—, —C(O)—, —OC(O)—, —C(O)O—, —OC(O)O—, —OC(O)NR$_1$—, —NR$_1$C(O)O—, —SC(O)—, and —C(O)S—;

$R_1$ is hydrogen or $C_1$ to $C_4$ alkyl;

each $B_1$ and $B_2$ is a divalent radical independently selected from the group consisting of aliphatic and aromatic carbocyclic and heterocyclic groups having 1 to 16 carbon atoms; optionally having one or more fused rings and optionally mono- or polysubstituted with L;

L is selected from the group consisting of the substituents F, Cl, —CN, and —NO$_2$; and alkyl, alkoxy, alkylcarbonyl, and alkoxycarbonyl groups, having 1 to 8 carbon atoms, wherein one or more of the carbon atoms are optionally substituted with F or Cl;

$A_1$ is a divalent linear or branched alkyl having 2 to 20 carbon atoms, optionally interrupted by linking groups selected from the group —O—, —S—, —C(O)—, —OC(O)— and —C(O)O—;

$A_2$ is a divalent linear or branched alkyl having 3 to 20 carbon atoms, optionally interrupted by linking groups selected from the group —O—, —S—, —C(O)—, —OC(O)— and —C(O)O—;

R is selected from the group consisting of hydrogen, F, Cl, —CN, —NO$_2$, and a monovalent linear or branched alkyl having 1 to 20 carbon atoms, optionally interrupted by linking groups selected from the group —O—, —S—, —C(O)—, —OC(O)— or —C(O)O—;

$R_p$ is a polymerizable group;

p and q are each independently an integer of 1 or 2; and r and t are each independently an integer of 0 or 1;

provided that when R is hydrogen, F, Cl, —CN, or —NO$_2$, and r is 1, $S_5$ is a covalent bond; and when R is hydrogen, F, Cl, —CN, or —NO$_2$, and r is 0, $S_3$ is a covalent bond.

Another embodiment of the invention is a polymerizable liquid crystal composition comprising at least one compound of formula (I) as defined above. A further embodiment is a polymer network derived from polymerization of the liquid crystal composition comprising at least one compound of formula (I) as defined above; and more specifically, a polymer network that reflects LHCPL. Another embodiment is an optical element comprising the polymer network defined above.

The terms (meth)acrylate salt, (meth)acrylate ester, (meth)acrylate acid, and the like, herein encompass materials and the moieties comprising the radical CH$_2$=C(R$_2$)—C(O)—O—; including methacrylate, wherein R$_2$ is methyl; acrylate, wherein R$_2$ is hydrogen; chloroacrylate, wherein R$_2$ is Cl; and fluoroacrylate, wherein R$_2$ is F; unless specifically defined otherwise.

DETAILED DESCRIPTION

The ability of a twisted nematic phase, which is also referred to herein as a cholesteric phase or a chiral nematic phase, to selectively reflect light in the infrared, visible or ultraviolet region is useful in many applications. When the propagation direction of plane polarized or unpolarized light is along the helical axis of the twisted nematic layer, the wavelength of maximum reflection, $\lambda_0$, is governed by the equation $\lambda_0 = n_a p$, wherein $n_a$ is the average of $n_o$ and $n_e$, and $n_o$ and $n_e$ are defined as the ordinary and extraordinary refractive indices, respectively, of the twisted nematic phase measured in the propagation direction; and wherein p is the pitch of the helix (the distance the helix takes to repeat itself). Light outside the vicinity of $\lambda_0$ is essentially unaffected in transmission. For light with a wavelength in the vicinity of wavelength $\lambda_0$, the twisted nematic phase exhibits selective reflection of the light such that approximately 50% of the light is reflected and approximately 50% of the light is transmitted, with both the reflected and transmitted beams being substantially circularly polarized. The pitch p can be tuned effectively by manipulating the amount of chiral dopant, the twisting power of the dopant and selection of the nematic materials. The pitch is sensitive to temperature, unwinding or tightening with a change in temperature; to electric fields, dopants, and other environmental considerations. Thus, in the twisted nematic phase, manipulation of the pitch, and thus the wavelength of maximum reflection, can be accomplished with a wide variety of tools.

Depending upon the intrinsic rotatory sense of the helical nature of the twisted nematic substance, i.e. whether it is right-handed or left-handed, the light that is transmitted is either right-hand circularly polarized light (RHCPL) or left-hand circularly polarized light (LHCPL). In order to conform to popular convention, twisted nematic liquid crystal substances will be hereinbelow identified by the kind of light that is reflected in the wavelength region around $\lambda_0$. When a cholesteric or twisted nematic layer is said to be right-handed it is meant that it reflects RHCPL, and when a layer is said to be left-handed it is meant that it reflects LHCPL. A right-handed nematic liquid crystal layer transmits LHCPL essentially completely, whereas the same layer reflects RHCPL almost completely, at $\lambda_0$. This assumes, of course, the cholesteric or twisted nematic layer is optimally aligned in a planar orientation. Conversely a left-handed nematic liquid crystal layer transmits RHCPL essentially completely, whereas the same layer reflects LHCPL almost completely, at $\lambda_0$. Since plane polarized or unpolarized light contains equal amounts of RHCPL and LHCP, a twisted nematic layer is approximately 50 percent transmitting at $\lambda_0$ for these light sources. This assumes, of course, the cholesteric or twisted nematic layer is optimally aligned in a planar orientation.

In certain optical applications, e.g. solar control applications, it is preferred that substantially all the light at some wavelengths be reflected. This requires at least one layer of each handedness, i.e. a layer reflecting RHCPL and a layer reflecting LHCPL, to be present. One method for reflecting substantially all of the light in the vicinity of $\lambda_0$ is to use two twisted nematic layers with similar $\lambda_0$, one right-handed and one left-handed. Light in the region around $\lambda_0$ transmitted by the first layer will be reflected by the second layer, with the result that substantially all of the incident light with a wavelength in the vicinity of $\lambda_0$ will be reflected. In theory, this may be accomplished by using enantiomeric chiral dopants of opposite chirality in matched twisted nematic layers. However, in most cases, one or both chiral dopants of the pair are usually very expensive, or unavailable. Thus, it is necessary to seek out suitable chiral dopants that have good compatibility with nematic phases, have high HTP, and may be used for the formation of right-handed nematic layers and left-handed nematic layers. Although the suitability of isosorbide based esters to induce chiral nematic phases that reflect RHCPL, and the suitability of isomannide based esters to induce chiral nematic phases that reflect LHCPL, is discussed in sources such as Strohriegl et al, in Adv. Mater. (2000), 12, (22) 1698-1670; U.S. Pat. No. 5,788,880; and U.S. Pat. No. 6,723,395; a need remains for crosslinking chiral monomers that have high HTP, have good phase compatibility with polymerizable nematic phases, and have the ability to induce a twisted nematic phase that reflect RHCPL or LHCPL.

One embodiment of the inventions disclosed herein is a compound as represented by the structure of the following formula (I):

$$R(S_5A_1)_r(S_3B_1)_pS_1\text{-}D\text{-}S_2(B_2S_4)_q(A_2S_6)_tR_p \quad (I)$$

wherein

D is the divalent moiety derived from isomannide:

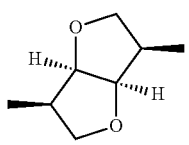

$S_1$ and $S_2$ are linking groups each independently selected from the group consisting of —O—, —OC(O)—, and —OC(O)O—;

$S_3$, $S_4$, $S_5$, and $S_6$, are linking groups each independently selected from the group consisting of covalent bond, —O—, —S—, —C(O)—, —OC(O)—, —C(O)O—, —OC(O)O—, —OC(O)NR$_1$—, —NR$_1$C(O)O—, —SC(O)—, and —C(O)S—;

$R_1$ is hydrogen or $C_1$ to $C_4$ alkyl;

each $B_1$ and $B_2$ is a divalent radical independently selected from the group consisting of aliphatic and aromatic carbocyclic and heterocyclic groups having 1 to 16 carbon atoms; optionally having one or more fused rings and optionally mono- or polysubstituted with L;

L is selected from the group consisting of the substitutents F, Cl, —CN, and —NO$_2$; and alkyl, alkoxy, alkylcarbonyl, and alkoxycarbonyl groups, having 1 to 8 carbon atoms, wherein one or more of the carbon atoms are optionally substituted with F or Cl;

$A_1$ is a divalent linear or branched alkyl having 2 to 20 carbon atoms, optionally interrupted by linking groups selected from the group —O—, —S—, —C(O)—, —OC(O)— and —C(O)O—;

$A_2$ is a divalent linear or branched alkyl having 3 to 20 carbon atoms, optionally interrupted by linking groups selected from the group —O—, —S—, —C(O)—, —OC(O)— and —C(O)O—;

R is selected from the group consisting of hydrogen, F, Cl, —CN, —NO$_2$, and a monovalent linear or branched alkyl having 1 to 20 carbon atoms, optionally interrupted by linking groups selected from the group —O—, —S—, —C(O)—, —OC(O)— or —C(O)O—;

$R_p$ is a polymerizable group;

p and q are each independently an integer of 1 or 2; and r and t are each independently an integer of 0 or 1;

provided that when R is hydrogen, F, Cl, —CN, or —NO$_2$, and r is 1, $S_5$ is a covalent bond; and when R is hydrogen, F, Cl, —CN, or —NO$_2$, and r is 0, $S_3$ is a covalent bond.

In formula (I), the left side of the formulas listed for $S_1$ and $S_2$ are connected to the isomannide radical. In a preferred embodiment $S_1$ and $S_2$ are —OC(O)—. The term "optionally interrupted by linking groups selected from the group —O—, —S—, —C(O)—, —OC(O)— or —C(O)O—" means that $A_1$, $A_2$, and R include alkyl radicals that have one or more of said linking groups, and if present, preferably have 1 to 3 said linking groups; provided that only one linking group, including linking groups $S_3$, $S_4$, $S_5$, and $S_6$, is bonded to any one alkyl carbon atom, and there are no linking groups bonded to each other. Examples of a suitable $A_1$ and $A_2$ divalent radicals that contain one or more linking groups are polyoxyalkylene chains, of the formula —(CH$_2$CH$_2$O)$_m$CH$_2$CH$_2$— wherein m is an integer of 1 to 9. Examples of a suitable R monovalent radicals that contain one or more linking groups are monoalkoxy-terminated poly(ethylene glycol) radicals of the formula $R_1$O—(CH$_2$CH$_2$O)$_m$CH$_2$CH$_2$— wherein m is an integer of 1 to 8, and $R_1$ is a $C_1$ to $C_4$ alkyl.

In one embodiment —$R_p$ is selected from the group consisting of CH$_2$=C(R$_2$)—, glycidyl ether, propenyl ether, oxetane, and 1,2-, 1,3-, and 1,4-substituted styryl and alkyl substituted styryl radicals, wherein R$_2$ is hydrogen, Cl, F, CN, or CH$_3$. Preferably —$R_p$ is CH$_2$=C(R$_2$)—, and R$_2$ is hydrogen or CH$_3$. A preferred embodiment is wherein t=0, the radical —S$_4$—R$_p$ is CH$_2$=C(R$_2$)—C(O)—O—, and R$_2$ is hydrogen or —CH$_3$. Another preferred embodiment is wherein t=1, and the radical —S$_6$—R$_p$ is CH$_2$=C(R$_2$)—C(O)—O—, and R$_2$ is hydrogen or —CH$_3$.

The term "each $B_1$ and $B_2$ is a divalent radical independently selected from the group" means that when p=2, the two $B_1$ units are selected independently, that is they may be the same or different; and when q=2, the two $B_2$ units are selected independently, that is they may be the same or different. Preferably $B_1$ and $B_2$ are selected from the group consisting of:

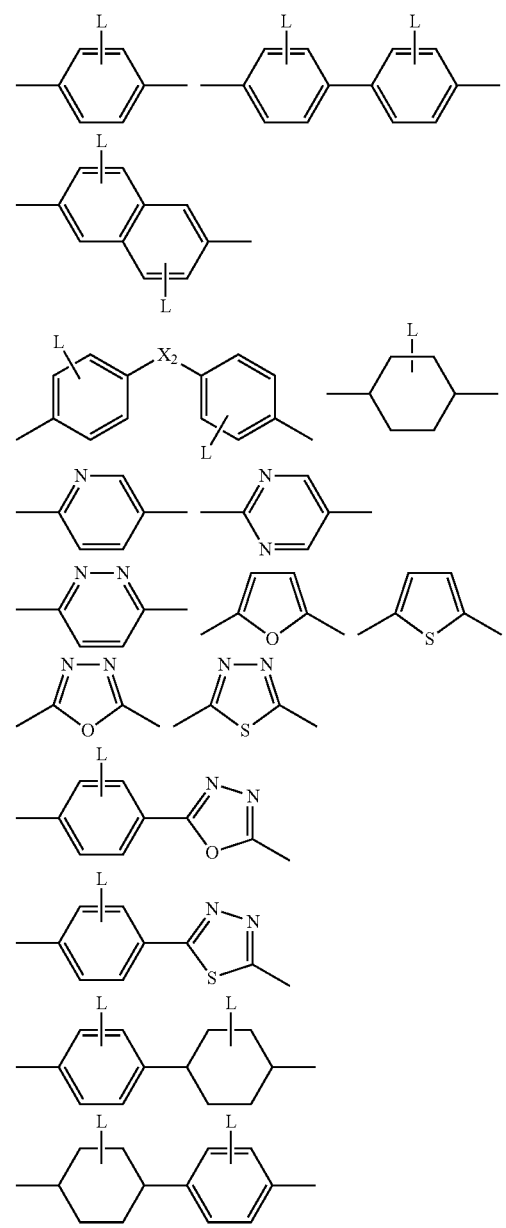

-continued

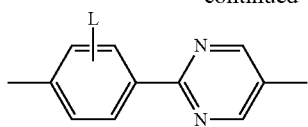

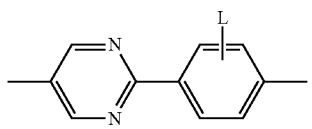

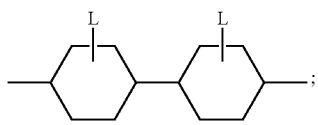

wherein $X_2$ is a divalent radical selected from the group: —O—, —(CH$_3$)$_2$C—, and —(CF$_3$)$_2$C—; and L is as defined above.

In a preferred embodiment $B_1$ and $B_2$ are each independently divalent radicals selected from the group consisting of 1,4-cyclohexyl; 2,6-naphthyl; 4,4'-biphenyl; and $R_{11}$-substituted-1,4-phenyl, wherein $R_{11}$ is H, —CH$_3$ or —OCH$_3$. The term "$R_{11}$-substituted-1,4-phenyl" refers to the radical

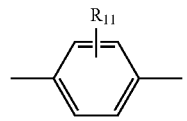

wherein $R_{11}$ can be bonded to any one of the four available carbon atoms. An especially preferred embodiment is wherein $B_1$ and $B_2$ are each independently the divalent radicals $R_{11}$-substituted-1,4-phenyl.

Another embodiment is compounds wherein, referring to formula (I), $S_1$ and $S_2$ are each —OC(O)—; p and q are each an integer of 1; $B_1$ and $B_2$ are each $R_{11}$-substituted-1,4-phenyl; $S_3$ is a covalent bond or —O—; t and r are each 0; $S_4$ is —OC(O)—; —$R_p$ is CH$_2$=C($R_2$)—; and R is a linear or branched C$_1$-C$_{20}$ alkyl. Compounds of this preferred group are represented by formula (II):

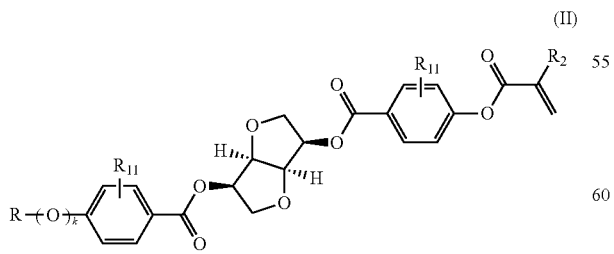

(II)

wherein k is 0 or 1; and $R_{11}$ and $R_2$ are as described above.

Compounds of formula (II) can be made by the synthesis pathway outlined in Scheme 1:

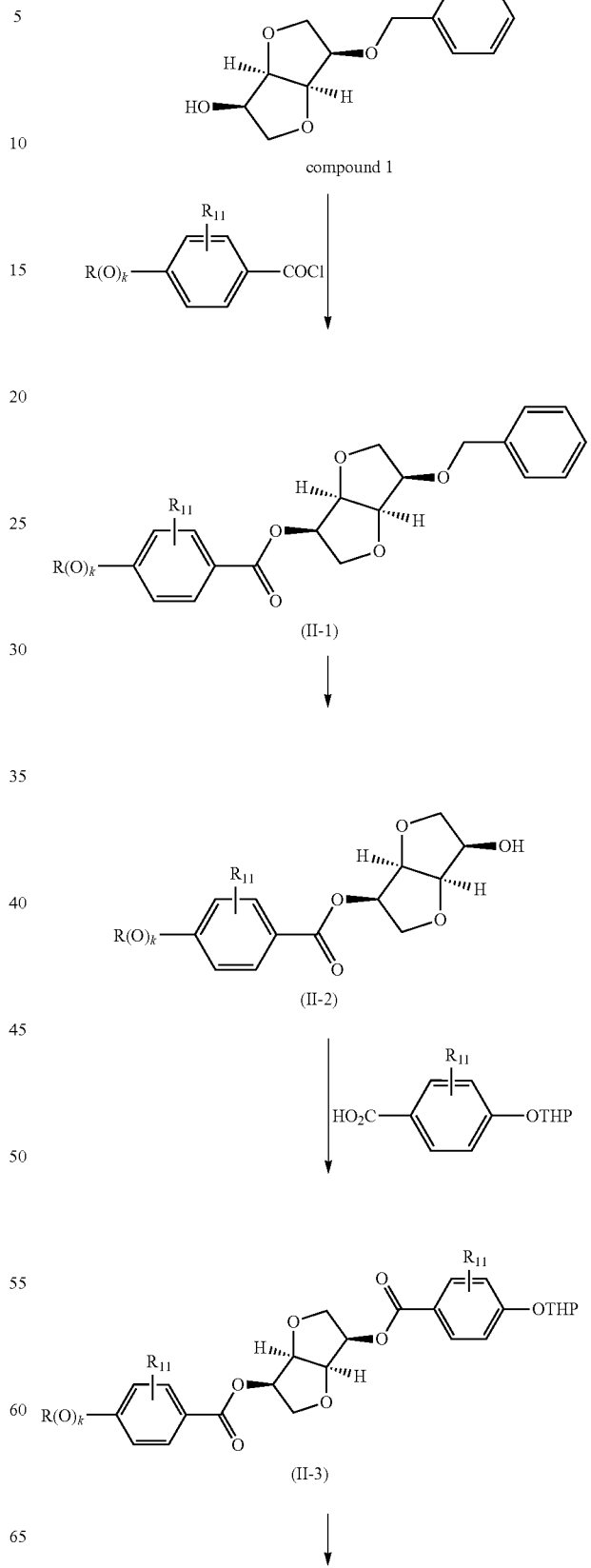

Scheme 1

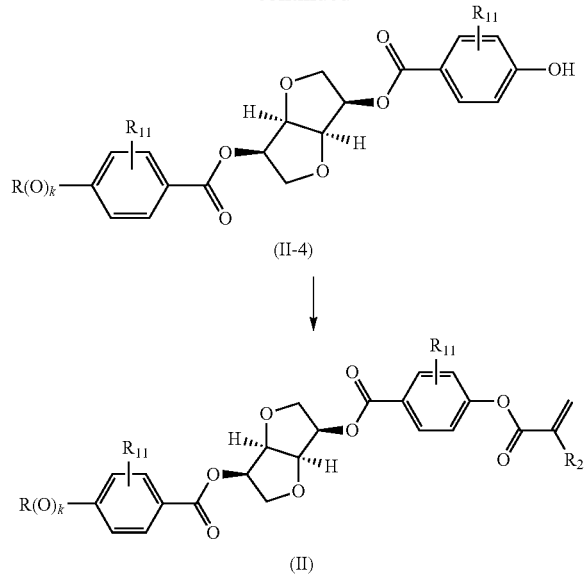

(II-4)

↓

(II)

Compound 1 is first acylated with a 4-substituted benzoyl chloride, to provide esters of Formula (II-1), followed by deprotection of the benzyl group with catalytic hydrogenation to provide alcohols of formula (II-2). Coupling of the alcohols of formula (II-2) with a 4-(2-tetrahydropyranyloxy) benzoic acid, optionally substituted with $R_{11}$, in the presence of a carbodiimide coupling agent and base provides compounds of formula (II-3). Compounds of formula (II-3) are deprotected with mild acid treatment to provide phenols of formula (II-4). The phenols can be acylated with meth(acryloyl) chlorides in the presence of base to provide the desired compounds of formula (II). The specific conditions for the syntheses are well known and exemplified in the examples herein. Table 1 lists some preferred compositions of formula (II).

TABLE 1

| No. | R | k | $R_{11}{}^a/R_{11}{}^b$ | $R_2$ |
|---|---|---|---|---|
| (IIa) | $CH_3$ | 1 | H/H | H |
| (IIb) | $CH_3$ | 1 | H/H | $CH_3$ |
| (IIc) | $CH_3$ | 0 | H/H | H |
| (IId) | $CH_3$ | 0 | H/H | $CH_3$ |
| (IIe) | $C_2H_5$ | 1 | H/H | H |
| (IIf) | $C_2H_5$ | 1 | H/H | $CH_3$ |
| (IIg) | $C_2H_5$ | 0 | H/H | H |
| (IIh) | $C_2H_5$ | 0 | H/H | $CH_3$ |
| (IIi) | $C_4H_9$ | 1 | H/H | H |
| (IIj) | $C_4H_9$ | 1 | H/H | $CH_3$ |
| (IIk) | $C_4H_9$ | 0 | H/H | H |
| (IIm) | $C_4H_9$ | 0 | H/H | $CH_3$ |
| (IIn) | $C_6H_{13}$ | 1 | H/H | H |
| (IIo) | $C_6H_{13}$ | 1 | H/H | $CH_3$ |
| (IIp) | $C_6H_{13}$ | 0 | H/H | H |
| (IIq) | $C_6H_{13}$ | 0 | H/H | $CH_3$ |
| (IIr) | $C_8H_{17}$ | 1 | H/H | H |
| (IIs) | $C_8H_{17}$ | 1 | H/H | $CH_3$ |
| (IIt) | $C_8H_{17}$ | 0 | H/H | H |
| (IIu) | $C_8H_{17}$ | 0 | H/H | $CH_3$ |

Another embodiment is a compound wherein, referring to formula (I), $S_1$ and $S_2$ are each —OC(O)—; p and q are each an integer of 1; $B_1$ and $B_2$ are each $R_{11}$-substituted-1,4-phenyl; $S_3$ is a covalent bond or —O—; r is 0; t is 1; $S_4$ and $S_6$ are each —OC(O)—; $A_2$ is divalent linear or branched $C_3$-$C_{20}$ alkylene; —$R_p$ is $CH_2$=C($R_2$)—; R is a linear or branched $C_1$-$C_{20}$ alkyl; and —$R_p$ is $CH_2$=C($R_2$)—. Compounds of this preferred group are represented by formula (III):

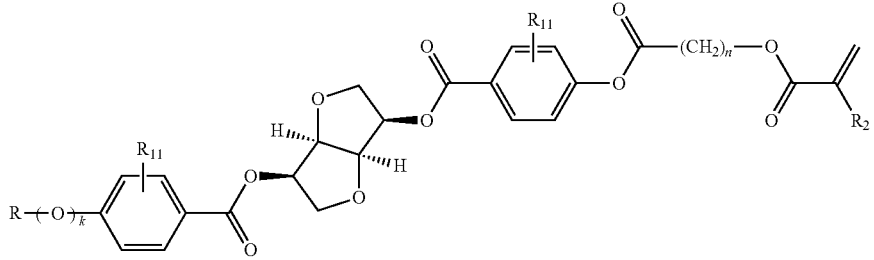

(III)

wherein k is 0 or 1, n is an integer of 3 to 20, and $R_{11}$ and $R_2$ are as described above.

Compounds of formula (III) can be made by the synthesis pathway outlined in Scheme 2:

Scheme 2

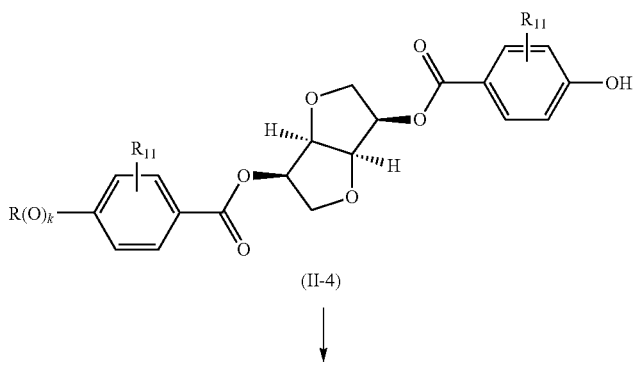

(II-4)

↓

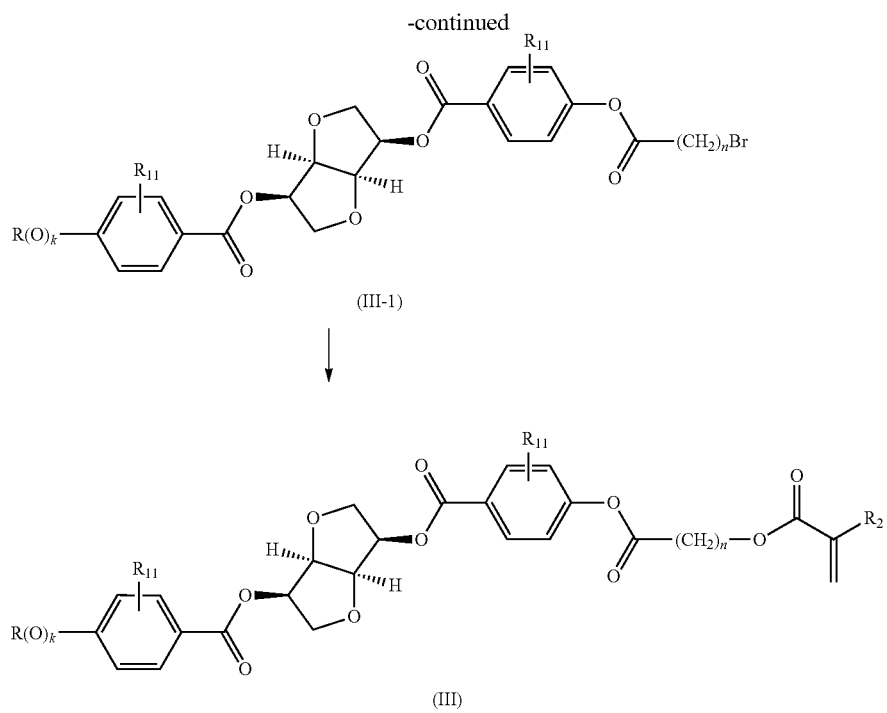

(III-1)

↓

(III)

Phenols of formula (II-4) are first acylated with an omega-bromoalkyl acid chloride in the presence of base to provide bromides of formula (III-1); followed by treatment with potassium meth(acrylate) and a phase transfer catalyst to provide the desired meth(acrylates) of formula (III). The specific conditions for the syntheses are exemplified in the examples herein. Table 2 lists several specific preferred compounds of formula (III).

TABLE 2

| No. | R | k | n | $R_{11}{}^a/R_{11}{}^b$ | $R_2$ |
|---|---|---|---|---|---|
| (IIIa) | $CH_3$ | 1 | 3 | H/H | H |
| (IIIb) | $CH_3$ | 1 | 5 | H/H | $CH_3$ |
| (IIIc) | $CH_3$ | 0 | 3 | H/H | H |
| (IIId) | $CH_3$ | 0 | 5 | H/H | $CH_3$ |
| (IIIe) | $C_2H_5$ | 1 | 3 | H/H | H |
| (IIIf) | $C_2H_5$ | 1 | 5 | H/H | $CH_3$ |
| (IIIg) | $C_2H_5$ | 0 | 3 | H/H | H |
| (IIIh) | $C_2H_5$ | 0 | 5 | H/H | $CH_3$ |
| (IIIi) | $C_4H_9$ | 1 | 3 | H/H | H |
| (IIIj) | $C_4H_9$ | 1 | 5 | H/H | $CH_3$ |

TABLE 2-continued

| No. | R | k | n | $R_{11}{}^a/R_{11}{}^b$ | $R_2$ |
|---|---|---|---|---|---|
| (IIIk) | $C_4H_9$ | 0 | 3 | H/H | H |
| (IIIm) | $C_4H_9$ | 0 | 5 | H/H | $CH_3$ |
| (IIIi) | $C_6H_{13}$ | 1 | 3 | H/H | H |
| (IIIj) | $C_6H_{13}$ | 1 | 5 | H/H | $CH_3$ |
| (IIIk) | $C_6H_{13}$ | 0 | 3 | H/H | H |
| (IIIm) | $C_6H_{13}$ | 0 | 5 | H/H | $CH_3$ |
| (IIIi) | $C_8H_{17}$ | 1 | 3 | H/H | H |
| (IIIj) | $C_8H_{17}$ | 1 | 5 | H/H | $CH_3$ |
| (IIIk) | $C_8H_{17}$ | 0 | 3 | H/H | H |
| (IIIm) | $C_8H_{17}$ | 0 | 5 | H/H | $CH_3$ |

$^{a,b}$refer to the various $R_{11}$ in formula (III)

Another embodiment are compounds wherein, referring to formula (I), $S_1$ and $S_2$ are each —OC(O)—; p is 1 and q is 2; $B_1$ and $B_2$ are each $R_{11}$-substituted-1,4-phenyl; $S_3$ is a covalent bond or —O—; t and r are each 0; $S_4$ is —OC(O)—; —$R_p$ is $CH_2$=$C(R_2)$—; and R is a linear or branched $C_1$-$C_{20}$ alkyl. Compounds of this preferred group are represented by formula (IV):

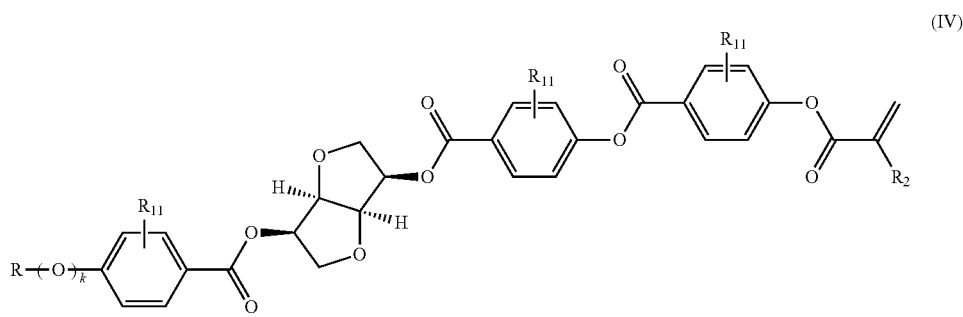

(IV)

wherein k is 0 or 1, and $R_{11}$, and $R_2$, are a described above.

Compounds of formula (IV) can be made by the synthesis pathway outlined in Scheme 3:
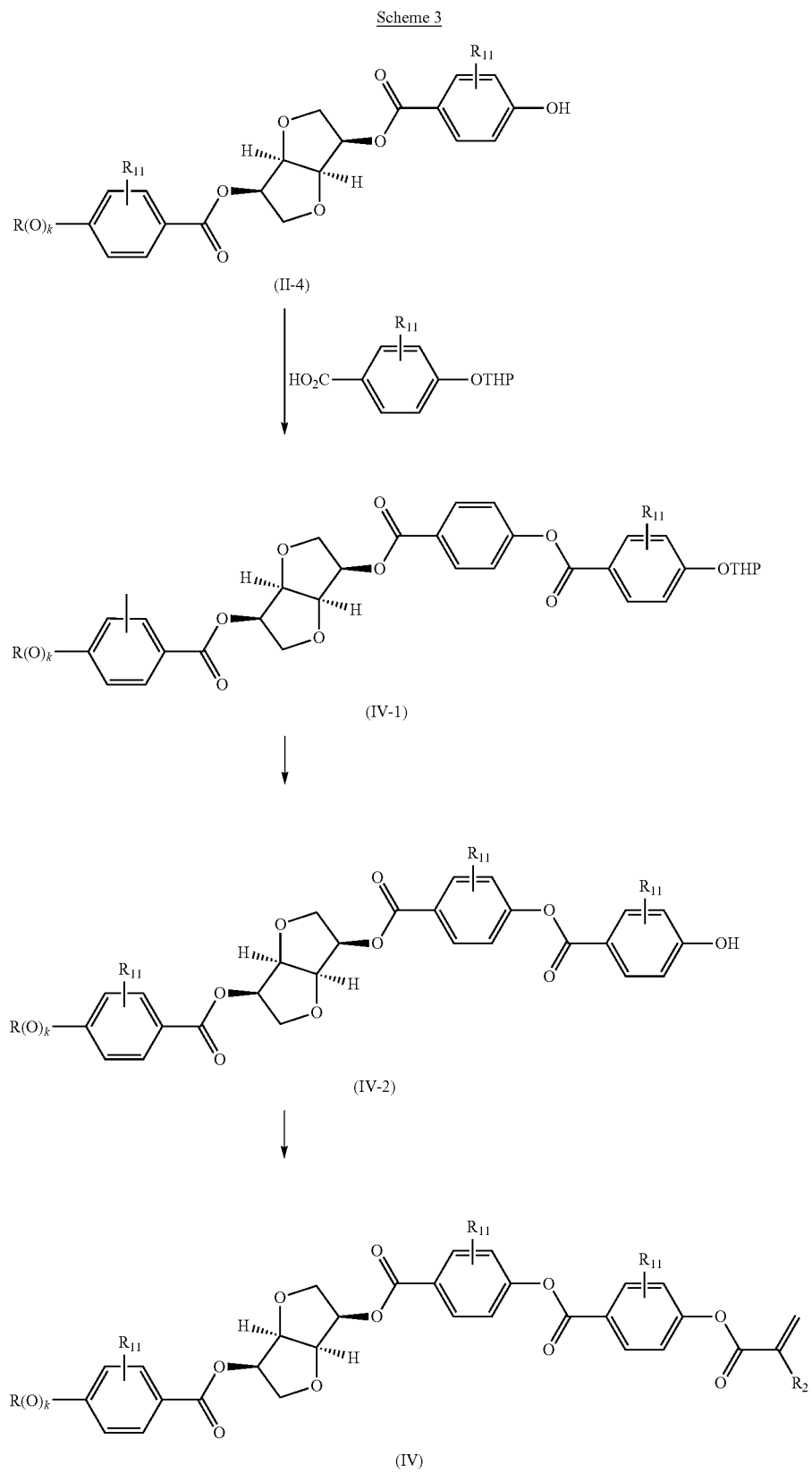

Coupling of the phenols of formula (II-4) with a 4-(2-tetrahydropyranyloxy)benzoic acid, optionally substituted with $R_{11}$, in the present of a carbodiimide coupling agent and base provides compounds of formula (IV-1). Compounds of formula (IV-1) are deprotected with mild acid treatment to provide phenols of formula (IV-2). The phenols (IV-2) can be acylated with meth(acryloyl) chlorides in the presence of base to provide the desired compounds of formula (IV). The general conditions for the syntheses are well known and exemplified in the examples herein. Table 3 lists several compounds of formula (IV).

lent bond or —O—; r is 0; t is 1; $S_4$ and $S_6$ are each —OC(O)—; $A_2$ is divalent linear or branched $C_3$-$C_{20}$ alkylene; $S_4$ is —OC(O)—, —$R_p$ is $CH_2$=$C(R_2)$—, and R is a linear or branched $C_1$-$C_{20}$ alkyl. Compounds of this preferred group are represented by formula (V) in Scheme 4 wherein k is 0 or 1, n is an integer of 3 to 20, and $R_{11}$ and $R_2$, are as described above:

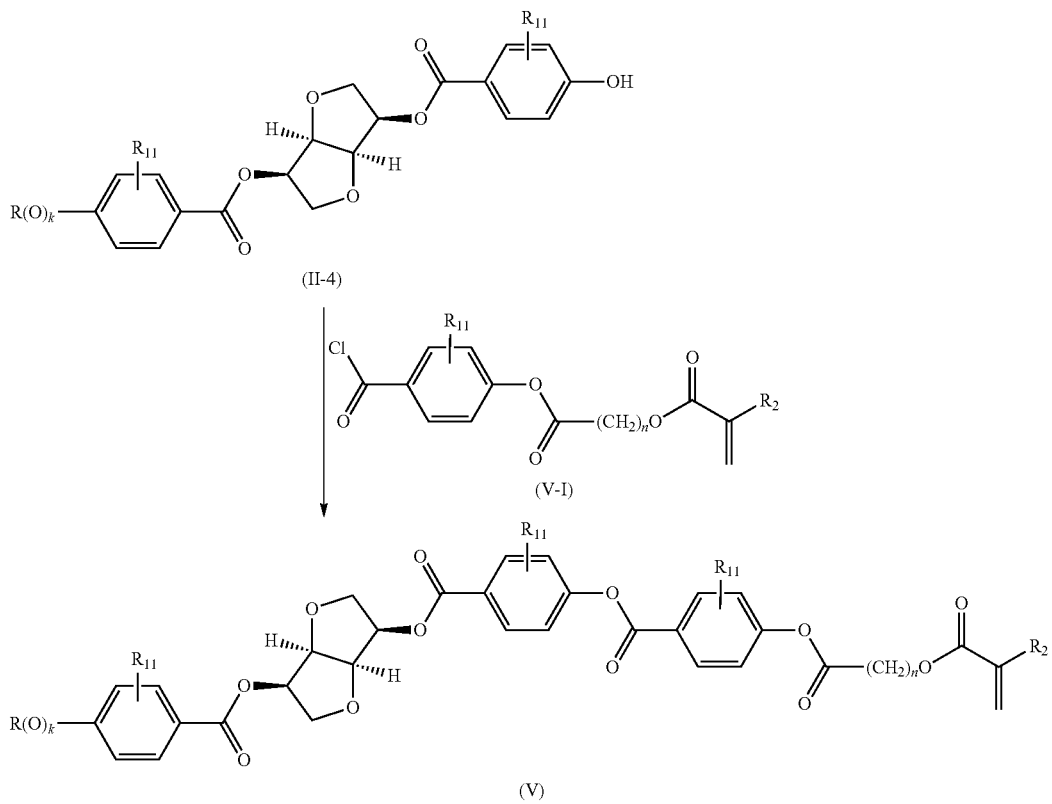

Scheme 4.

Compounds of formula (V) can be made by the synthesis pathway outlined in Scheme 4. Phenols of formula (II-4) are acylated with an acid chloride (V-1) in the presence of base to provide the desired meth(acrylates) of formula (V). The specific conditions for the syntheses are exemplified in the examples herein. Table 4 lists several compounds of formula (V).

TABLE 3

| No. | R | k | $R_{11}{}^a$/$R_{11}{}^b$/$R_{11}{}^c$ | $R_2$ |
|---|---|---|---|---|
| (IVa) | $CH_3$ | 1 | H/H/H | H |
| (IVb) | $CH_3$ | 1 | H/H/H | $CH_3$ |
| (IVc) | $CH_3$ | 0 | H/H/H | H |
| (IVd) | $CH_3$ | 0 | H/H/H | $CH_3$ |
| (IVe) | $C_6H_{13}$ | 1 | H/H/H | H |
| (IVf) | $C_6H_{13}$ | 1 | H/H/H | $CH_3$ |
| (IVg) | $C_6H_{13}$ | 0 | H/H/H | H |
| (IVh) | $C_6H_{13}$ | 0 | H/H/H | $CH_3$ |
| (IVi) | $C_8H_{17}$ | 1 | H/H/H | H |
| (IVj) | $C_8H_{17}$ | 1 | H/H/H | $CH_3$ |
| (IVk) | $C_8H_{17}$ | 0 | H/H/H | H |
| (IVm) | $C_8H_{17}$ | 0 | H/H/H | $CH_3$ |

$a,b,c$refer to the various $R_{11}$ in formula (IV)

Another embodiment are compounds wherein, referring to formula (I), $S_1$ and $S_2$ are each —OC(O)—; p is 1 and q is 2; $B_1$ and $B_2$ are each $R_{11}$-substituted-1,4-phenyl; $S_3$ is a cova-

TABLE 4

| No. | R | k | n | $R_{11}{}^a$/$R_{11}{}^b$/$R_{11}{}^c$ | $R_2$ |
|---|---|---|---|---|---|
| (Va) | $CH_3$ | 1 | 5 | H/H/H | H |
| (Vb) | $CH_3$ | 1 | 3 | H/H/H | $CH_3$ |
| (Vc) | $CH_3$ | 0 | 5 | H/H/H | H |
| (Vd) | $CH_3$ | 0 | 3 | H/H/H | $CH_3$ |
| (Ve) | $C_6H_{13}$ | 1 | 5 | H/H/H | H |
| (Vf) | $C_6H_{13}$ | 1 | 3 | H/H/H | $CH_3$ |
| (Vg) | $C_6H_{13}$ | 0 | 5 | H/H/H | H |
| (Vh) | $C_6H_{13}$ | 0 | 3 | H/H/H | $CH_3$ |
| (Vi) | $C_8H_{17}$ | 1 | 5 | H/H/H | H |
| (Vj) | $C_8H_{17}$ | 1 | 3 | H/H/H | $CH_3$ |
| (Vk) | $C_8H_{17}$ | 0 | 5 | H/H/H | H |
| (Vm) | $C_8H_{17}$ | 0 | 3 | H/H/H | $CH_3$ |

$a,b,c$refer to the various $R_{11}$ in formula (V)

Another embodiment are compounds wherein, referring to formula (I), $S_1$ and $S_2$ are each —OC(O)—; p is 2 and q is 1; $B_1$ and $B_2$ are each $R_{11}$-substituted-1,4-phenyl; $S_5$ is a covalent bond or —O—; t and r are each 0; $S_3$ is —OC(O)—; —$R_p$ is $CH_2$=$C(R_2)$—; and R is a linear or branched $C_1$-$C_{20}$ alkyl. Compounds of this preferred group are represented by formula (VI):

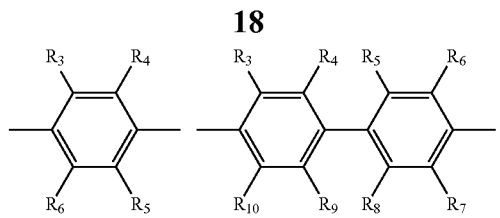

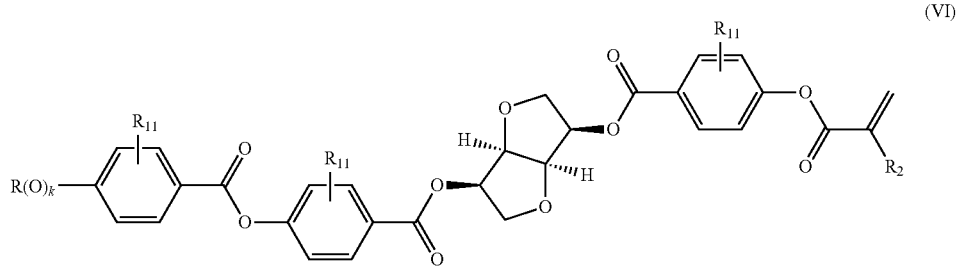

(VI)

wherein k is 0 or 1, and $R_{11}$ and $R_2$, are as described above. Compounds of formula (VI) can be made by synthesis from compound 1 using the synthetic methods similar to those outlined in Scheme 3.

Compounds of formula (I) are useful in polymerizable liquid crystal compositions, also of the invention. Compounds of formula (I) are useful as chiral dopants to induce chirality of a nematic phase to provide a twisted nematic phase. Useful twisted nematic phases can be provided by mixing the chiral dopants at about 0.5 to about 30 wt % based on the total nematic mixture. Preferred embodiments are polymerizable liquid crystal compositions comprising at least one compound of formula (II); (III); (IV), (V); (VI); or a combination thereof.

A wide variety of polymerizable and nonpolymerizable liquid crystals can be used in the polymerizable liquid crystal compositions of the invention including in those disclosed in Makromol. Chem. 190, 2255-2268 (1989), Macromolecules, 1988, 31, 5940, Makromol. Chem. 192, 59-74 (1991), J. Polym. Sci.: Part A: Polym. Chem., Vol. 37, 3929-3935 (1999), and Makromol. Chem. 190, 3201-3215 (1989). Additional polymerizable monomers useful in liquid crystal compositions are disclosed in U.S. Pat. No. 5,833,880, DE 4408170, EP 261712, EP 331233 B1, EP 397263 B1, and WO1998047979, hereby incorporated by reference. A preferred group of polymerizable monomers for the polymerizable liquid crystal compositions of the invention are those of formula (VII):

-continued

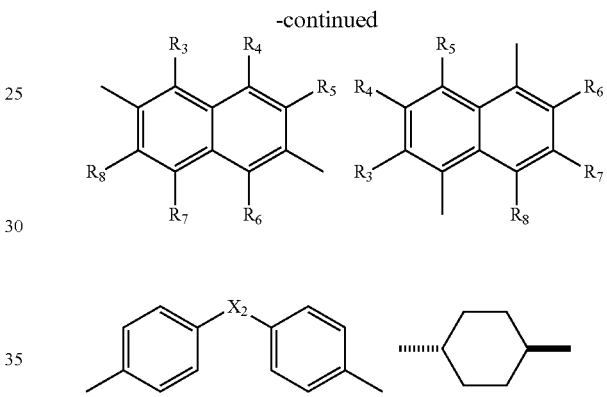

wherein $R_3$-$R_{10}$ are independently selected from the group: H, $C_1$-$C_8$ straight or branched chain alkyl, $C_1$-$C_8$ straight or branched chain alkyloxy, F, Cl, phenyl, —C(O)CH$_3$, CN, and CF$_3$;

$X_2$ is a divalent radical selected from the group: —O—, —(CH$_3$)$_2$C—, and —(CF$_3$)$_2$C—; and each $B_3$ and $B_4$ is a divalent radical independently selected from the group: 2,6-naphthyl; 4,4'-biphenyl; and $R_{11}$-substituted-1,4-phenyl, wherein $R_{11}$ is H, —CH$_3$ or —OCH$_3$;

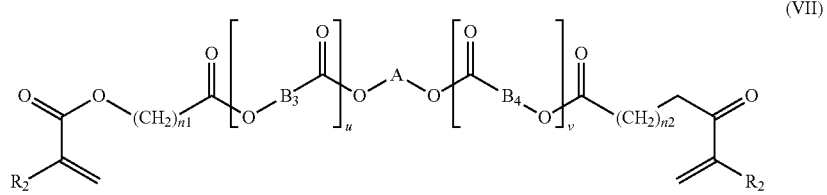

(VII)

wherein $R_2$ is independently selected from the group: H, F, Cl, and CH$_3$;

n1 and n2 are, independently, integers 3 to 20;

u and v are, independently, integers 0, 1 or 2;

A is a divalent radical selected from the group:

with the proviso that when the sum of u+v is equal to 3 or 4, at least two of $B_3$ and $B_4$ are $R_{11}$-substituted-1,4-phenyl.

A preferred embodiment is a polymerizable liquid crystal composition of the invention comprising polymerizable monomers wherein, referring to formula (VII), u is 1 and v is 0, and formula (VII) is formula (VIIIa):

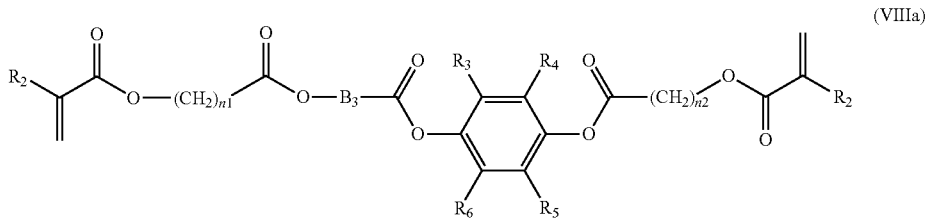

(VIIIa)

wherein $R_2$ is independently H or $CH_3$; $R_3$-$R_6$ are independently H or —$CH_3$; n1 and n2 are independently integers of 3 to 20; and $B_3$ is $R_{11}$-substituted-1,4-phenyl, wherein $R_{11}$ is H, —$CH_3$ or —$OCH_3$.

Another preferred embodiment is a polymerizable liquid crystal composition of the invention comprising polymerizable monomers wherein, referring to formula (VII), u and v are 1, and formula (VII) is formula (IXa):

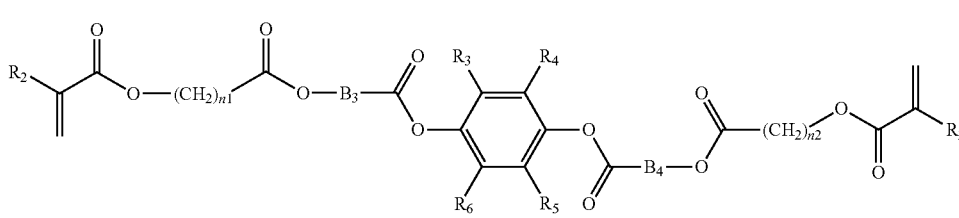

(IXa)

wherein $R_2$ is independently H or $CH_3$; $R_3$-$R_6$ are independently H or —$CH_3$; n1 and n2 are independently integers of 3 to 20; and $B_3$ and $B_4$ are $R_{11}$-substituted-1,4-phenyl, wherein $R_{11}$ is H, —$CH_3$ or —$OCH_3$. Another preferred embodiment is a polymerizable liquid crystal composition of the invention comprising a mixture of polymerizable monomers of formula (VIIIa) and (IXa).

The synthesis of compounds of formula (VII), (VIIIa) and (IXa), and liquid crystal mixtures thereof, is disclosed in pending U.S. application Ser. No. 11/731,289, which is incorporated in its entirety as a part hereof for all purposes. The synthesis of Compounds 25, 26 and 27, disclosed below, are specific examples of monomers of formula (IXa) and (VIIIa) that are used in the examples illustrating the preparation of polymerizable liquid crystal compositions. Preferred polymerizable liquid crystal compositions of the invention have a twisted nematic phase below 120° C.

The liquid crystal compositions of the invention are useful in preparing polymer networks that exhibit the fixed optical properties of twisted nematic polymer networks. The polymer network of the invention is one or more polymerized layer(s) comprising a liquid crystal composition that include: polymerized films, coatings, castings and prints; including patterned, unpatterned, variable and nonvariable optical properties; that can be made by a wide variety of methods as disclosed, for instance, in U.S. Pat. Nos. 4,637,896, 6,010,643 and 6,410,130.

In particular, one preferred method for making a polymer network comprises: providing a polymerizable twisted nematic mixture, in the form of a twisted nematic or isotropic phase, with a polymerization initiator, preferably a radical initiator; applying the twisted nematic mixture to one or more substrates, optionally the substrate(s) comprises an alignment layer, to provide a layer of the twisted nematic mixture; optionally treating the layer to provide a desired twisted nematic phase; and polymerizing the twisted nematic phase, preferably by exposing the twisted nematic phase to actinic radiation.

The liquid crystal compositions of various embodiments of the invention can include a radical initiator, and preferably the radical initiator is a photoinitiator useful in conducting photochemical polymerizations. For curing by electron beams, such initiators are not required. Examples of suitable photoinitiators are isobutyl benzoin ether, 2,4,6-trimethylbenzoyl-diphenylphosphine oxide, 1-hydroxycyclohexyl phenyl ketone, 2-benzyl-2-dimethylamino-1-(4-morpholinophenyl) furan-1-one, mixtures of benzophenone and 1-hydroxycyclohexyl phenyl ketone, 2,2-dimethoxy-2-phenylacetophenone, perfluorinated diphenyltitanocenes, 2-methyl-1-(4-[methylthio]phenyl)-2-(4-morpholinyl)-1-propanone, 2-hydroxy-2-methyl-1-phenylpropan-1-one, 4-(2-hydroxyethoxy)phenyl 2-hydroxy-2-propyl ketone, 2,2-diethoxyacetophenone, 4-benzoyl-4'-methyldiphenyl sulfide, ethyl 4-(dimethylamino)benzoate, mixtures of 2-isopropylthioxanthone and 4-isopropylthioxanthone, 2-(dimethylamino)ethyl benzoate, d,1-camphorquinone, ethyl-d,1-camphorquinone, mixtures of benzophenone and 4-methylbenzophenone, benzophenone, 4,4'-bisdimethylaminobenzophenone, triphenylsulfonium hexafluorophosphate or mixtures of triphenylsulfonium salts. Preferably the photoinitiators are present at a level of about 0.1 wt % to 3 wt % of the polymerizable liquid crystal mixture.

As a substrate, for example, a glass or quartz sheet, as well as a plastic film or sheet can be used. It is also possible to put a second substrate on top of the coated mixture prior to, during and/or after polymerization. The substrates can optionally be removed after polymerization. When using two substrates in the case of curing by actinic radiation, at least one substrate should be transmissive for the polymerization. Isotropic or birefringent substrates can be used. In case the substrate is not removed from the polymerized film after polymerization, preferably isotropic substrates are used.

Preferably at least one substrate is a plastic substrate, for example, a film of polyester such as polyethylene terephthalate (PET), of polyvinylalcohol (PVA), polycarbonate (PC) or triacetylcellulose (TAC), especially preferably a PET film or a TAC film. As a birefringent substrate, for example, an uniaxially stretched plastic film can be used. Preferably the substrates are buffed with a buffing clothe to enhance alignment of the chiral nematic phase.

Applying the twisted nematic mixture can be accomplished by any method that gives a uniform layer, or if desired, a patterned or non-uniform layer. Coating, including rod-coating, extrusion coating, gravure coating, slot-die coating and spin-coating, spraying, printing, blading, knifing, or a combination of methods, can be used.

Preferably the polymerizable liquid crystal mixture is coated as a thin layer on a substrate or between substrates, and aligned in its chiral mesophase into planar orientation, wherein the axis of the molecular helix extends transversely to the layer. Planar orientation can be achieved, for example, by shearing the mixture, e.g., by means of a doctor blade. It is also possible to put a second substrate on top of the coated material. In this case, the shearing caused by putting together the two substrates is sufficient to give good alignment. Alternatively it is possible to apply an alignment layer, for example a layer of rubbed polyimide or sputtered $SiO_2$, on top of at least one of the substrates, or to apply an electric or magnetic field to the coated mixture, in order to induce or enhance planar alignment. Useful polyimide alignment layers are disclosed in U.S. Pat. No. 6,887,455. Alignment of twisted nematic phases by coating of dilute liquid crystal mixtures is disclosed in U.S. Pat. No. 6,410,130. Planar alignment may be induced or enhanced by addition of one or more surface-active compounds to the polymerizable mixture.

Treating the liquid crystal layer to provide a desired liquid crystal phase can include, cooling or heating the liquid crystal layer, for instance to achieve a desired phase or optical property; application of a mechanical shear to the liquid crystal layer, for instance, by application of a knife blade to the liquid crystal layer, shearing two or more substrates wherein the liquid crystal layer is interposed, or vibration, sonication or other form of agitation to the substrate(s).

Another method for making a polymer network involves providing an isotropic solution that contains a polymerizable liquid crystal mixture, a polymerization initiator, preferably a photoinitiator, and a carrier solvent; applying the isotropic solution to one or more substrate(s), preferably where the substrate(s) is an alignment layer, to provide an isotropic layer; removing the carrier solvent and, optionally, treating the layer, to provide a desired liquid crystal phase; and polymerizing the liquid crystal phase, preferably by exposing the liquid crystal phase to actinic radiation. U.S. Pat. Nos. 6,010,643 and 4,637,896 exemplify preparation of a liquid crystal layer using two substrates to form a cell. U.S. Pat. Nos. 4,637,896 and 6,410,130 exemplify preparation of a liquid crystal layer from an isotropic solution, followed by polymerization.

Where a carrier solvent is used with the liquid crystal composition, coating and spraying are preferred methods for applying the isotropic solution. Removing the carrier solvent can be accomplished by allowing the carrier solvent to evaporate, with or without heating and/or application of a vacuum. Allowing the carrier solvent to evaporate also may be accompanied and/or followed by application of a mechanical shear to the liquid crystal layer as described above. Examples of carrier solvents are linear or branched esters, especially acetic esters, cyclic ethers and esters, alcohols, lactones, aliphatic and aromatic hydrocarbons, such as toluene, xylene and cyclohexane, chlorinated hydrocarbons, such as dichloromethane, 1,1,2,2-tetrachloroethane, and also ketones, amides, N-alkylpyrrolidones, especially N-methylpyrrolidone. Additional examples of useful solvents include tetrahydrofuran (THF), dioxane, methyl ethyl ketone (MEK), and propylene glycol monomethyl ether acetate.

The liquid crystal compositions of the invention may further comprise small amounts of a polymerizable diluent including, for example, 2-ethoxyethyl acrylate, diethylene glycol diacrylate, ethylene glycol dimethacrylate, diethylene glycol dimethacrylate, triethylene glycol dimethacrylate, diethylene glycol monomethyl ether acrylate, phenoxyethyl acrylate, tetraethylene glycol dimethacrylate, pentaerythritol tetraacrylate and ethoxylated pentaerythritol tetraacrylate.

The liquid crystal compositions of the invention may further comprise small amounts of surfactants, leveling agents, viscosity modifiers, wetting agents, defoamers, and UV and radical stabilizers. Selection will often be based upon observed coating and alignment quality and the desired adhesion of the final polymer network to the substrate and other layers. Typical surfactants comprise siloxy-, fluoryl-, alkyl- and alkynyl-substituted surfactants. These include surfactants sold under the trade names BYK (Byk Chemie, Wesel, Germany), ZONYL (DuPont), TRITON (Dow Chemical Co., Midland, Mich.), SURFUNOL and DYNOL (Air Products, Inc. Allentown, Pa.). A stabilizer may be used to prevent undesired spontaneous polymerization, for example, during storage of the composition. A wide variety of stabilizers may be used for this purpose. Typical examples for stabilizers are 4-ethoxyphenol, 4-methoxyphenol, methyl hydroquinone, and butylated hydroxytoluene (BHT).

Exposing the liquid crystal phase to actinic radiation can be done by a variety of means, including heat, microwave radiation, UV and visible light, and electron beam and other radiation. Radiation sources can include Hg arc lamps, Xenon lamps, laser light sources, and the like. The exposing can be done selectively, if so desired, and may include the use of a mask, or a computer controlled scan system. A detailed description of the in situ polymerization of polymerizable mesogenic compounds can be found, for example, in D. J. Broer et al., Makromolekulare Chemie 190, 2255 (1989).

Polymerization is preferably carried out under an atmosphere of inert gas, preferably under a nitrogen atmosphere. The polymerization can be conducted at room temperature, below room temperature or above room temperature if so desired. The optical properties of a twisted nematic liquid crystal phase, particularly the wavelength of reflection, can be tuned, to some extent, by adjusting the temperature of the phase. In a preferred embodiment, the polymerization is conducted above room temperature (~25° C.), preferably about 40° C. to about 10° C. below the isotropic point of the liquid crystal composition. A preferred temperature range for conducting the polymerization is about 50° C. to about 90° C., provided this is below the isotropic point of the liquid crystal composition. The polymerization above room temperature generally provides a polymer network with a lower haze, as determined by visual observation, than one provided by polymerization at room temperature.

The polymer networks of the invention can be made either flexible or brittle depending on crosslinking. The brittle films can be flaked and the flakes used as pigments in a variety of inks or paints for use in cosmetics and automobile paint. The films can be combined with other pigments or pigment layers, for instance black layers, that act to enhance the brilliance of the reflected light.

The polymer networks of the invention are useful as optical elements or components of an optical element. An optical element is any film, coating or shaped object that is used to modify the characteristics of light. The modifications produced by optical elements include changes in the intensity of light through changes in transmission or reflectivity, changes in wavelength or wavelength distribution, changes in the state of polarization, changes in the direction of propagation of part or all of the light, or changes in the spatial distribution of intensity by, for example, focusing, collimating, or diffusing the light. Examples of optical elements include linear polarizers, circular polarizers, lenses, mirrors, collimators, diffusers, reflectors and the like. One specific example of an optical element is a layer of a cholesteric polymer network of the invention that reflects light within the vicinity of $\lambda_o$, employed in a window structure.

A particular valuable attribute of the chiral monomers of the invention is their ability to induce a twisted nematic phase that reflects LHCPL. The handedness of reflected light can be determined according to well known procedures described in W. A. Shurcliff, "Polarized Light: Production and Use", Harvard University Press, (1962). Polymer networks of the invention that incorporated a chiral dopant based on the isomannide compounds of formula (I) reflected LHCPL. Thus, another embodiment of the invention is a polymer network that reflects LHCPL. Another embodiment is a polymer network that reflects LHCPL, and has a wavelength of maximum reflection in the range of about 280 nm to about 2000 nm; and more preferably, in the range of about 700 nm to about 1200 nm.

EXAMPLES

This invention is further defined in the following examples. It should be understood that these examples, while indicating preferred embodiments of the invention, are given by way of illustration only. The selection of the embodiments set forth below to illustrate the inventions hereof does not indicate that materials, components, reactants, ingredients, conditions or designs not described in these examples are not suitable for practicing these inventions, or that subject matter not described in these examples is excluded from the scope of the appended claims and equivalents thereof.

In the examples, thermal transitions are given in degrees Centigrade. The following notations are used to describe the observed phases: K=crystal, N=nematic, S=smectic, TN*=twisted nematic, X=unidentified phase, I=isotropic, P=polymerized. The thermal transitions and phase assignments were made with differential scanning calorimetry and hotstage optical microscopy. Unless stated otherwise, phase behavior is reported for the first heating. The following abbreviations are used in the examples:
DCM=dichloromethane,
DMAc=dimethyl acetamide,
DMAP=4-dimethylamino pyridine,
DI water=deionized water,
EDC=1-ethyl-3-(3-dimethylaminopropyl)carbodiimide hydrochloride,
IPA=isopropyl alcohol,
mp=melting point,
pTSA=p-toluenesulfonic acid,
PPTS=pyridinium p-toluenesulfonate,
THF=tetrahydrofuran,
TEA=triethylamine,
THP=tetrahydropyranyl,
RT=room temperature.

For the examples, the following compounds were first prepared:

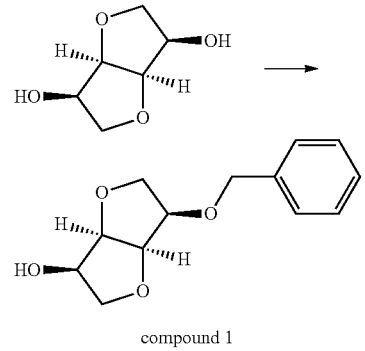

compound 1

To a mixture of isomannide (200 g), Ag$_2$O (159 g), and toluene (2.0 L) in a flask equipped with a mechanical stirrer was dropwise added benzyl bromide (179 mL). After stirring for 16 hrs at RT, the mixture was filtered and the filtrate was concentrated, washed with water, and recrystallized in hexanes/ethyl ether to provide Compound 1 (102 g): mp 91-92° C.; $^1$H NMR (DMSO-d$_6$, 500 MHz) δ 3.39 (t, J=8.5 Hz, 1H), 3.51 (t, J=8.4 Hz, 1H), 3.82 (dd, J=8.2, 6.9 Hz, 1H), 3.89 (dd, J=8.4, 6.9 Hz, 1H), 4.03-4.15 (br m, 2H), 4.30 (t, J=4.8 Hz, 1H), 4.48 (d, J=11.7 Hz, 1H), 4.53 (t, J=4.7, 1H), 4.62 (d, J=11.7 Hz, 1H), 4.73 (d, J=6.9 Hz, 1H), 7.23-7.42 (br m, 5H).

Compound 4 compound 4

To a mixture of p-hydroxybenzoic acid (20.1 g), PPTS (0.12 g) in DCM (80 mL) was added 3,4-dihydro-2H-pyran (14.6 mL). The reaction mixture was allowed to stir at RT overnight. The solution mixture was filtered, washed with ethyl ether, and dried to provide Compound 4 (19.0 g): $^1$H NMR (CDCl$_3$, 500 MHz) δ 1.62 (m, 1H), 1.70 (m, 2H), 1.89 (m, 2H), 2.01 (m, 1H), 3.63 (m, 1H), 3.86 (m, 1H), 5.52 (t, J=3.1 Hz, 1H), 7.10 (m, 2H), 8.06 (m, 2H), 10.1 (br s, 1H).

Compounds 25, 26 and 27 are liquid crystal monomers that were used in formulation of liquid crystal mixtures of the various embodiments of the invention. The syntheses of the monomers are disclosed in pending U.S. application Ser. No. 11/731,289, which is incorporated in its entirety as a part hereof for all purposes, and are illustrated in the following Schemes 5-7.

Scheme 5

Compound 25

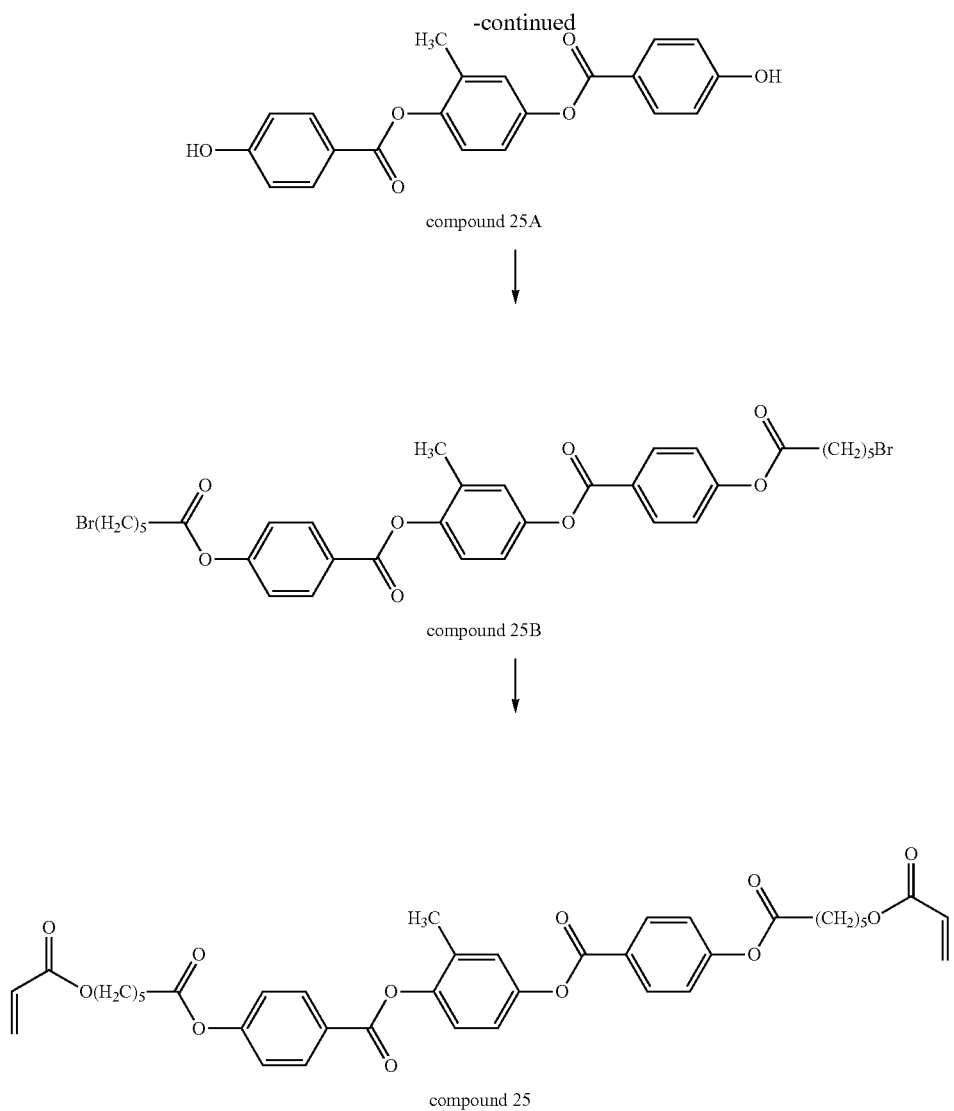

compound 25A compound 25B compound 25

A mixture of 4-hydroxybenzoic acid (240.0 g), methylhydroquinone (100.2 g), pTSA (6 g), and xylenes (1.5 L) was heated to reflux under a nitrogen atmosphere for a total of 26 h in a flask equipped with a Dean-Stark trap, condenser and mechanical stirrer. Additional pTSA (6.0 g portions) was added after 8 and 18 h after cooling the reaction mixture RT. The final reaction mixture was cooled to RT, the solids collected and washed with hexanes. The solids were slurried with hot acetone (600 mL) and cooled to RT, collected and dried to provide Compound 25A: $^1$H NMR (DMSO-d$_6$, 500 MHz) δ 2.16 (s, 3H), 6.93 (d, J=8.8 Hz, 2H), 6.95 (d, J=8.8 Hz, 2H), 7.13 (m, 1H), 7.23 (m, 2H), 7.99 (d, J=8.8 Hz, 2H), 8.02 (d, J=8.8 Hz, 2H), 10.51 (s, 2H).

A mixture of Compound 25A (100 g), THF (750 mL), and TEA (165 mL) was cooled to 0° C. A mixture of 6-bromohexanoyl chloride (126.0 g) in THF (400 mL) was added over about 0.75 h. The mixture was stirred at 0° C. for 2 h and allowed to warm to RT, and stirred for 2 h. The mixture was poured into water (1.5 L) and hydrochloric acid (37%) was added until the mixture was pH 6. The mixture was stirred for 15 min and the solids collected. The solids were rinsed with water, methanol and then dried to provide Compound 25B:

$^1$H NMR (CDCl$_3$, 500 MHz) δ 1.60 (m, 4H), 1.81 (m, 4H), 1.95 (m, 4H), 2.25 (s, 3H), 2.62 (t, J=7.4 Hz, 2H), 2.63 (t, J=7.4 Hz, 2H), 3.45 (t, J=6.8 Hz, 4H), 7.10 (dd, J=8.6, 2.7 Hz, 1H), 7.14 (d, J=2.7, 1H), 7.19 (d, J=8.6 Hz, 1H), 7.24 (d, J=8.7 Hz, 2H), 7.25 (d, J=8.7 Hz, 2H), 8.22 (d, J=8.7 Hz, 2H), 8.25 (d, J=8.7 Hz, 2H).

To a mixture of Compound 25B (20.0 g), potassium bicarbonate (25.1 g), tetrabutyl ammonium iodide (5.14 g), 2,6-di-tert-butyl-4-methylphenol (1.04 g), and THF (350 mL) was added acrylic acid (5.73 mL). The mixture was heated at 65° C. for 9 h and then allowed to stir at RT overnight. The mixture was partition between ethyl ether/water, and the ether layer washed with several portions of water. The ether layer was dried and the solvent removed and the product recrystalized from isopropanol to provide Compound 25 (17.25 g): $^1$H NMR (CDCl$_3$, 500 MHz) δ0.54 (m=4H), 1.77 (m, 4H), 1.83 (m, 4H), 2.25 (s, 3H), 2.624 (t, J=7.4 Hz, 2H), 2.629 (t, J=7.4 Hz, 2H), 4.21 (t, J=6.6, 4H), 5.82 (dd, J=10.4, 1.3 Hz, 2H), 6.13 (dd, J=17.3, 10.4 Hz, 2H), 6.40 (dd, J=17.3, 1.3 Hz, 2H), 7.10 (dd, J=8.7, 2.7 Hz, 1H), 7.15 (d, J=2.7, 1H), 7.19 (d, J=8.7, 1H), 7.24 (d, J=8.6 Hz, 2H), 7.25 (d, J=8.6 Hz, 2H), 8.22 (d, 8.6 Hz, 2H), 8.25 (d, J=8.6 Hz, 2H).

Scheme 6

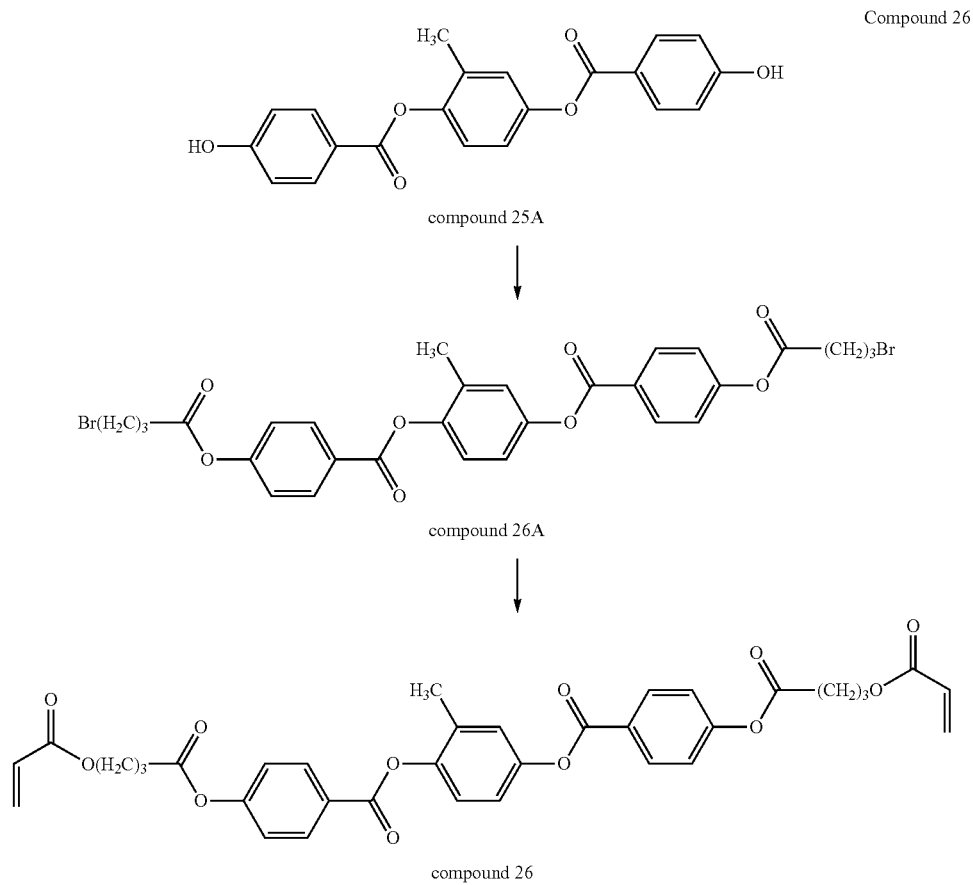

Using a similar procedure to that used for Compound 25B, Compound 25A was acylated with 4-bromobutyroyl chloride to provide Compound 26A, followed by displacement of the bromides with acrylate to provide Compound 26: $^1$H NMR (CDCl$_3$, 500 MHz) δ 2.17 (m, 4H), 2.26 (s, 3H), 2.73 (t, J=7.3 Hz, 2H), 2.74 (t, J=7.3 Hz, 2H), 4.308 (t, J=6.2 Hz, 2H), 4.310 (t, J=6.2 Hz, 2H), 5.858 (dd, J=10.5, 1.4 Hz, 1H), 5.860 (dd, J=10.5, 1.4 Hz, 1H), 6.144 (dd, J=17.4, 10.5 Hz, 1H), 6.146 (dd, J=17.4, 10.5 Hz, 1H), 6.434 (dd, J=17.4, 1.4 Hz, 1H), 6.437 (dd, J=17.4, 1.4 Hz, 1H), 7.10 (dd, J=8.6, 2.8 Hz, 1H), 7.15 (d, J=2.6, 1H), 7.19 (d, J=8.8 Hz, 1H), 7.25 (d, J=8.8 Hz, 2H), 7.27 (d, J=8.8 Hz, 2H), 8.23 (d, J=8.8 Hz, 2H), 8.26 (d, J=8.8 Hz, 2H).

Scheme 7

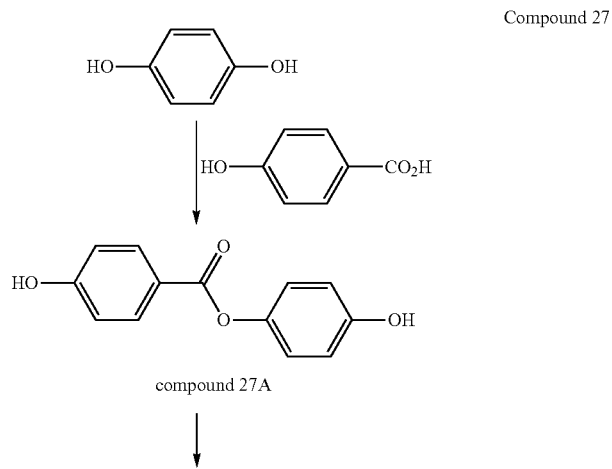

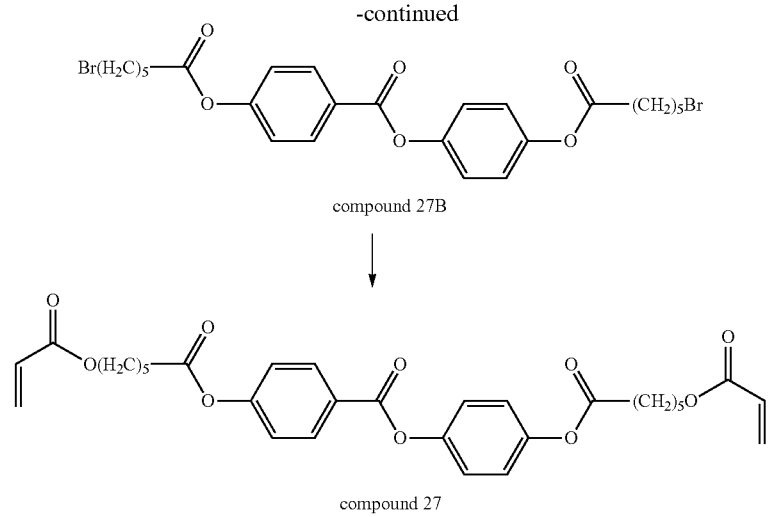

compound 27B

↓ compound 27

A mixture of 4-hydroxybenzoic acid (80 g), hydroquinone (64 g), pTSA (2 g), xylenes (500 mL) was heated to reflux in a flask equipped with a Dean-Stark trap, condenser and mechanical stirrer until about 10 mL of water were collected. After cooling to room temperature the solids were filtered off, washed with hexanes, and dried. The solids were placed into 600 mL of boiling acetone and stirred for 30 min. The mixture was filtered hot to eliminate traces of insoluble material. After cooling to RT, DI water (1500 mL) was added slowly to precipitate the product. The precipitated product was filtered off and dried to provide Compound 27A. $^1$H NMR (CDCl$_3$, 500 MHz) δ 6.78 (d, 8.9 Hz, 2H), 6.90 (d, J=8.8 Hz, 2H), 7.00 (d, J=8.9 Hz, 2H), 7.94 (d, J=8.8 Hz, 2H), 9.42 (s, 1H), 10.44 (s, 1H).

Compound 27B was prepared using an analogous procedure as was described above for the synthesis of Compound 25B. $^1$H NMR (CDCl$_3$, 500 MHz) δ1.59 (m, 4H), 1.80 (m, 4H), 1.94 (m, 4H), 2.59 (t, J=7.4 Hz, 2H), 2.63 (t, J=7.4 Jz, 2H), 3.441 (t, J=6.7 Hz, 2H), 3.446 (t, J=6.7 Hz, 2H), 7.14 (d, J=9.0 Hz, 2H), 7.22 (d, 9.0 Hz, 2H), 7.24 (d, 8.8 Hz, 2H), 8.22 (d, 8.8 Hz, 2H).

Compound 27 was prepared using an analogous procedure as was described above for the synthesis of Compound 25. $^1$H NMR (CDCl$_3$, 500 MHz) δ 1.52 (m, 4H), 1.76 (m, 4H), 1.78 (m, 4H), 2.59 (t, J=7.4 Hz, 2H), 2.62 (t, J=7.4 Hz, 2H), 4.19 (t, J=6.6 Hz, 2H), 4.20 (t, J=6.6 Hz, 2H), 5.823 (dd, 1H), 5.826 (dd, 1H), 6.122 (dd, 1H), 6.127 (dd, 1H), 6.404 (dd, 1H), 6.407 (dd, 1H), 7.13 (d, J=8.6 Hz, 2H), 7.21 (d, J=8.6 Hz, 2H), 7.23 (d, J=8.6 Hz, 2H), 8.21 (d, J=8.6 Hz, 2H).

Example 1

This example illustrates the synthesis of Compound 7 according to Scheme 8:

Scheme 8

Compound 1

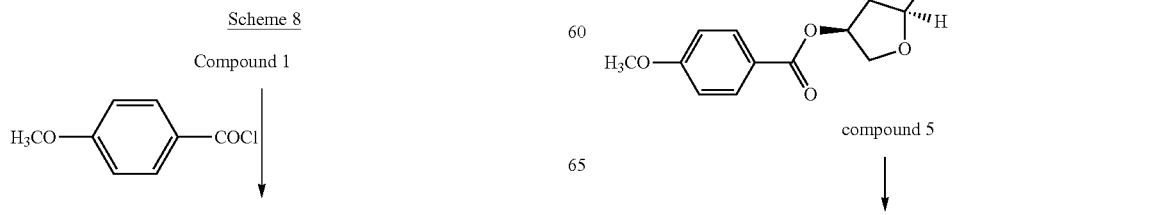

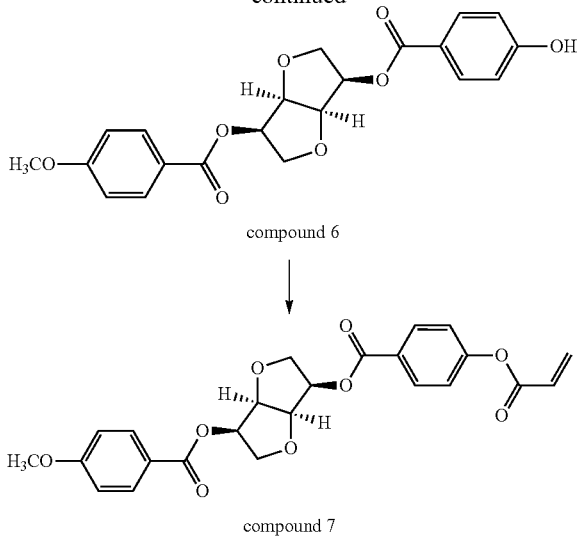

compound 6 compound 7

2H), 4.14 (m, 2H), 4.88 (m, 2H), 5.33 (m, 2H), 6.08 (br s, 1H), 6.85 (m, 2H), 6.92 (m, 2H), 7.98 (m, 2H), 8.05 (m, 2H).

A mixture of Compound 6 (5.00 g) and TEA (7.0 mL) in THF (180 mL) was cooled to 0° C. A mixture of acryloyl chloride (2.03 mL) in THF (25 mL) was added dropwise. The reaction mixture was allowed to stir at 0° C. for 30 min and at RT for 1 h. The reaction mixture was filtered, acidified with 0.5 M HCl solution, extracted with DCM. The combined organic layer was washed with water, dried with anhydrous MgSO$_4$, filtered, and concentrated to provide Compound 7 (4.57 g): mp 95-96° C.; $^1$H NMR (CDCl$_3$, 500 MHz) δ 3.87 (s, 3H), 4.00 (m, 2H), 4.14 (dd, J=9.4, 6.3 Hz, 2H), 4.87 (m, 2H), 5.30-5.36 (br m, 2H), 6.06 (dd, J=10.4, 1.2 Hz, 1H), 6.33 (dd, J=17.3, 10.5 Hz, 1H), 6.63 (dd, 17.3, 1.2 Hz, 1H), 6.93 (m, 2H), 7.24 (m, 2H), 8.05 (m, 2H), 8.14 (m, 2H).

Example 2

This example illustrates the synthesis of Compound 12 according to Scheme 9:

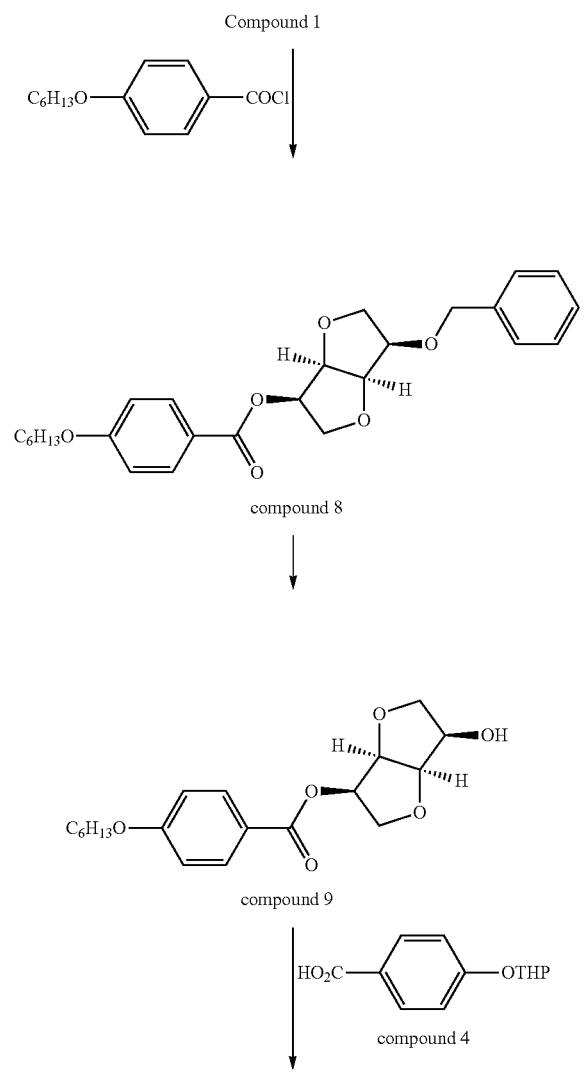

Scheme 9

A mixture of Compound 1 (18.6 g), DMAP (9.62 g), and pyridine (100 mL) was cooled to 0° C. in an ice bath, followed by addition of p-methoxybenzoyl chloride (11.7 mL). After stirring at 0° C. for 30 min and at RT for 1 h, the mixture heated to 80° C. for 5 h. After cooling to RT, the mixture was concentrated, acidified with 0.5 M HCl solution, and extracted with DCM. The combined organic layer was washed with 0.1 M NaOH solution, water, dried with anhydrous MgSO$_4$, filtered and concentrated. The crude mixture was recrystallized in hexanes to provide Compound 2 (23.6 g): $^1$H NMR (CDCl$_3$, 500 MHz) δ 3.69 (t, J=8.8 Hz, 1H), 3.85 (s, 3H), 3.92 (dd, J=8.5, 6.9 Hz, 1H), 4.07 (m, 1H), 4.11 (d, J=5.8 Hz, 2H), 4.53 (t, J=4.0 Hz, 1H), 4.59 (d, J=11.9 Hz, 1H), 4.77 (d, J=11.9 Hz, 1H), 4.81 (t, J=5.2 Hz, 1H), 5.33 (dt, J=5.8, 5.8 Hz, 1H), 6.91 (m, 2H), 7.27-7.42 (br m, 5 Hz), 8.02 (m, 2H).

Compound 2 (40.0 g) was dissolved in THF/IPA (1:1, 250 mL) followed by addition of Pd(OH)$_2$ on activated carbon (20 wt % of Pd on the dry basis) (4.0 g). The reaction mixture was stirred at RT under H$_2$ for 4 h (at 1.7 atm). The mixture was filtered and concentrated to provide Compound 3 (29.6 g): $^1$H NMR (CDCl$_3$, 500 MHz) δ 2.67 (d, J=8.6 Hz, 1H), 3.61 (dd, J=9.2 Hz, 7.2 Hz, 1H), 3.86 (s, 3H), 3.97 (dd, J=9.2, 6.3 Hz, 1H), 4.01 (dd, J=9.5 Hz, 6.1 Hz, 1H), 4.20 (dd, J=9.6, 6.2 Hz, 1H), 4.30 (app qui, J=6.4 Hz, 1H), 4.53 (t, J=5.3 Hz, 1H), 4.81 (t, J=5.3 Hz, 1H), 5.37 (dt, J=5.9, 5.6 Hz, 1H), 6.92 (m, 2H), 8.03 (m, 2H).

To a mixture of Compound 4 (14.5 g), DMAP (4.62 g), and EDC (21.8 g), in DCM (500 mL), under nitrogen, was added slowly a solution of Compound 3 (10.6 g) in DCM (200 mL). The reaction mixture was allowed to stir at RT overnight. The solution mixture was concentrated, washed with 0.1 M HCl solution, 0.1 M NaOH solution, and water. The organic layer was dried, filtered and concentrated to provide Compound 5 (18.8 g): $^1$H NMR (CDCl$_3$, 500 MHz) δ 1.60 (m, 1H), 1.70 (m, 2H), 1.88 (m, 2H), 2.00 (m, 1H), 3.61 (dt, J=11.2, 4.0 Hz, 1H), 3.84 (m, 1H), 3.86 (s, 3H), 3.99 (m, 2H), 4.13 (dd, J=9.4, 6.4 Hz, 2H), 4.86 (m, 2H), 5.31 (m, 2H), 5.50 (t, J=3.1 Hz, 1H), 6.93 (m, 2H), 7.08 (m, 2H), 8.03 (m, 2H), 8.05 (m, 2H).

A mixture of Compound 5 (28.2 g) and pTSA (5.64 g) in THF/methanol (1:1, 800 mL) was stirred at RT overnight. The reaction mixture was concentrated, precipitated in water, filtered, and dried to obtain Compound 6 (19.3 g): $^1$H NMR (CDCl$_3$, 500 MHz) δ 3.86 (s, 3H), 4.01 (dd, J=9.4, 6.8 Hz,

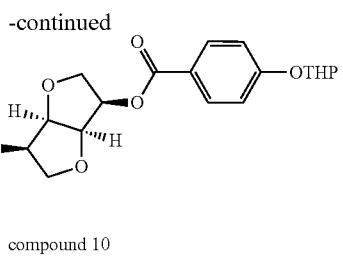

compound 10

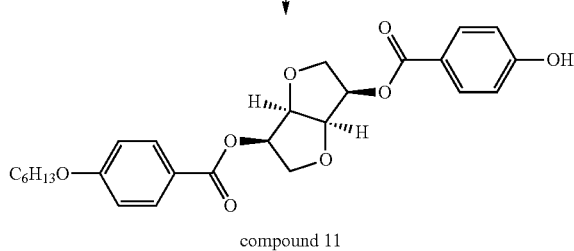

compound 11

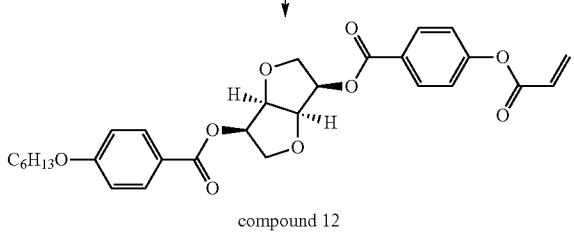

compound 12

A mixture of Compound 1 (4.67 g), DMAP (1.94 g) and pyridine (40 mL), under a nitrogen atmosphere, was cooled to 0° C. in an ice bath, followed by addition of 4-hexyloxybenzoyl chloride (5.0 mL). After stirring at 0° C. for 30 min and at RT for 1 h, the mixture heated to 80° C. for 6 h. After cooling to RT, the mixture was concentrated, acidified with 0.5 M HCl solution, and extracted with DCM. The combined organic layer was washed with 0.1 M NaOH solution, water, dried with anhydrous MgSO$_4$, filtered and concentrated. The crude mixture was precipitated in hexanes to provide Compound 8 (7.41 g): $^1$H NMR (CDCl$_3$, 500 MHz) δ 0.91 (t, J=7.1 Hz, 3H), 1.34 (m, 4H), 1.46 (m, 2H), 1.79 (m, 2H), 3.69 (t, J=8.7 Hz, 1H), 3.92 (dd, J=8.5, 6.9 Hz, 1H), 4.00 (t, J=6.6 Hz, 2H), 4.07 (m, 1H), 4.11 (d, J=5.8 Hz, 2H), 4.53 (t, J=4.9 Hz, 1H), 4.59 (d, 11.8 Hz, 1H), 4.77 (d, 11.8 Hz, 1H), 4.81 (t, J=5.3 Hz, 1H), 5.33 (q, J=5.8 Hz, 1H), 6.89 (m, 2H), 7.27-7.41 (br m, 5H), 8.01 (m, 2H).

Compound 8 (4.20 g) was dissolved in THF/IPA (1:1, 7 mL) followed by addition of Pd(OH)$_2$ on activated carbon (20 wt % of Pd on the dry basis) (0.63 g). The mixture was stirred at RT under H$_2$ for 2 h. The solution mixture was filtered and concentrated to provide Compound 9 (2.47 g): $^1$H NMR (CDCl$_3$, 500 MHz) δ 0.91 (t, J=7.0 Hz, 3H), 1.34 (m, 4H), 1.46 (m, 2H), 1.80 (m, 2H), 2.63 (br d, J=7.5 Hz, 1H), 3.61 (dd, J=9.1, 7.2 Hz, 1H), 3.98 (m, 2H), 4.01 (t, J=6.5 Hz, 2H), 4.20 (dd, J=9.5, 6.2 Hz, 1H), 4.31 (app qui, J=6.1 Hz, 1H), 4.53 (t, J=5.3 Hz, 1H), 4.81 (t, J=5.2 Hz, 1H), 5.37 (dt, J=6.1, 5.7 Hz, 1H), 6.91 (m, 2H), 8.01 (m, 2H).

To a mixture of Compound 4 (1.01 g) and Compound 9 (1.00 g) in DCM (30 mL) under nitrogen, a mixture of EDC (1.70 g) and DMAP (0.35 g) in DCM (5 mL) was slowly added. The mixture was allowed to stir at RT overnight. The mixture was washed with 0.1 M HCl solution, 0.1 M NaOH solution, and water. The organic layer was dried with anhydrous MgSO$_4$, filtered and concentrated to provide the crude product. The crude material was purified by silica flash chromatography eluting with a mixture of ethyl acetate in hexane (10%-50% in gradient) to provide Compound 10 (0.96 g): $^1$H NMR (CDCl$_3$, 500 MHz) δ 0.91 (t, J=8.0 Hz, 3H), 1.34 (m, 4H), 1.47 (m, 2H), 1.61 (m, 1H), 1.70 (m, 2H), 1.80 (m, 2H), 1.88 (m, 2H), 2.01 (m, 1H), 3.62 (m, 1H), 3.85 (m, 1H), 3.98 (m, 2H), 4.01 (t, J=6.4 Hz, 2H), 4.13 (dd, J=11.4, 8.3 Hz, 2H), 4.86 (m, 2H), 5.31 (m, 2H), 5.51 (t, J=3.9 Hz, 2H), 6.91 (m, 2H), 7.08 (m, 2H), 8.02 (m, 2H), 8.04 (m, 2H).

A solution mixture of Compound 10 (0.96 g) and pTSA (0.19 g) in THF/methanol (1:1, 25 mL) was stirred at RT overnight. The mixture was concentrated, precipitated in water, filtered, and dried to obtain Compound 11 (0.73 g): $^1$H NMR (CDCl$_3$, 500 MHz) δ 0.91 (t, J=7.0 Hz, 3H), 1.34 (m, 4H), 1.47 (m, 2H), 1.80 (m, 2H), 4.00 (m, 2H), 4.01 (t, J=6.5 Hz, 2H), 4.14 (dt, J=9.4, 6.6 Hz, 2H), 4.87 (m, 2H), 5.32 (m, 2H), 6.86 (m, 2H), 6.91 (m, 2H), 7.99 (m, 2H), 8.03 (m, 2H).

A mixture of Compound 11 (0.50 g) and TEA (0.59 mL) in THF (15 mL) was cooled to 0° C. A mixture of acryloyl chloride (0.17 mL) in THF (5 mL) was added dropwise. The reaction mixture was allowed to stir at 0° C. for 30 min and at RT for 2 h. The reaction mixture was filtered, acidified with dilute HCl, extracted with DCM. The combined organic layer was washed with water, dried, filtered, concentrated, and precipitated in hexanes to provide Compound 12 (0.41 g): mp 83-84° C.; $^1$H NMR (CDCl$_3$, 500 MHz) δ 0.91 (t, J=7.0 Hz, 3H), 1.34 (br m, 4H), 1.47 (m, 2H), 1.80 (m, 2H), 3.99 (m, 2H), 4.01 (t, J=6.7 Hz, 2H), 4.14 (dd, J=9.4, 6.4 Hz, 2H), 4.87 (m, 2H), 5.32 (m, 2H), 6.05 (dd, J=10.5, 1.1 Hz, 1H), 6.33 (dd, J=17.3, 10.5 Hz, 1H), 6.63 (dd, J=17.3 Hz, 1.1 Hz, 1H), 6.91 (m, 2H), 7.24 (m, 2H), 8.03 (m, 2H), 8.14 (m, 2H).

Example 3

This example illustrates the synthesis of Compound 17 according to Scheme 10:

Scheme 10

Compound 1

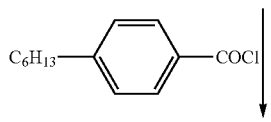

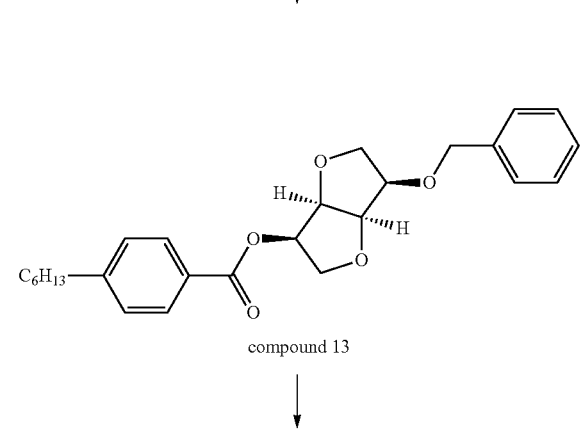

compound 13

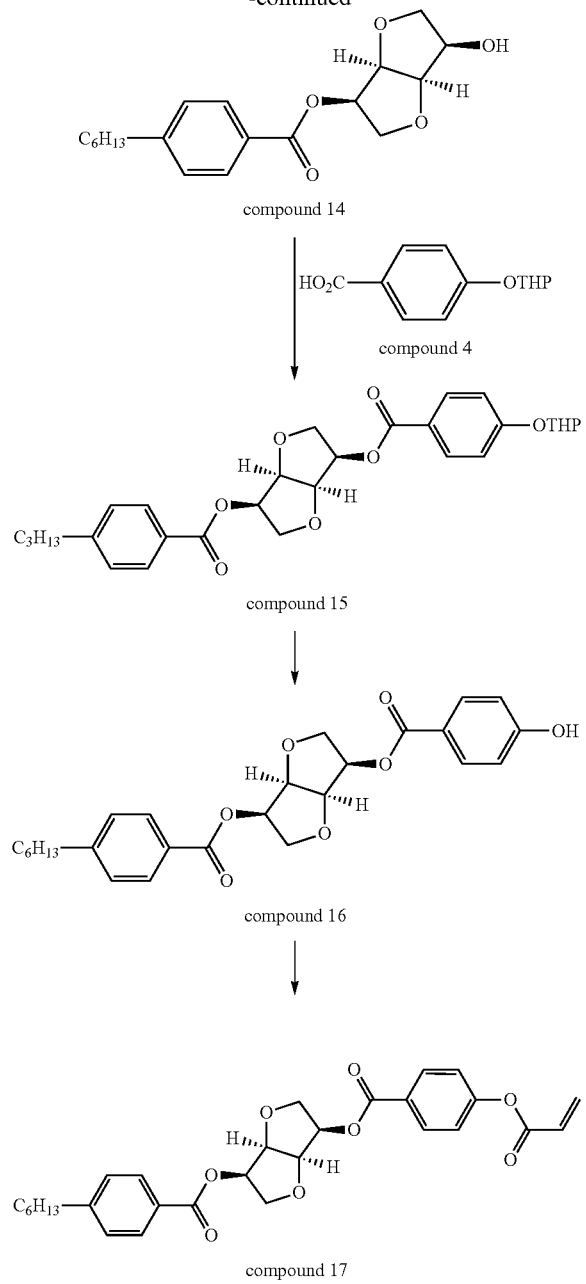

Compounds 13 through 17 were made in a similar manner to Compounds 8 through 12, but replacing 4-hexyloxybenzoyl chloride, with 4-hexylbenzoyl chloride.

Compound 13 (7.57 g): $^1$H NMR (CDCl$_3$, 500 MHz) δ 0.88 (t, J=6.9 Hz, 3H), 1.30 (m, 6H), 1.62 (m, 2H), 2.65 (t, J=7.7 Hz, 2H), 3.69 (t, J=8.7 Hz, 1H), 3.92 (dd, J=8.5, 6.9 Hz, 1H), 4.07 (m, 1H), 4.12 (d, J=5.8 Hz, 2H), 4.54 (t, J=4.9 Hz, 1H), 4.59 (d, J=11.9 Hz, 1H), 4.77 (d, J=11.9 Hz, 1H), 4.82 (t, J=5.3 Hz, 1H), 5.35 (dt, J=5.8, 5.7 Hz, 1H), 7.23 (m, 2H), 7.27-7.40 (br m, 5H), 7.98 (m, 2H).

Compound 13 (7.57 g) was hydrogenated for 5 h to provide Compound 14 (4.91 g). $^1$H NMR (CDCl$_3$, 500 MHz) δ 0.88 (t, J=6.9 Hz, 3H), 1.30 (m, 6H), 1.62 (m, 2H), 2.62 (br s, 1H), 2.66 (t, J=7.7 Hz, 2H), 3.61 (dd, J=9.1, 7.2 Hz, 1H), 3.97 (dd, J=9.2, 6.3 Hz, 1H), 4.02 (dd, J=9.6, 6.1 Hz, 1H), 4.20 (dd, J=9.6, 6.2 Hz, 1H), 4.32 (app qui, J=6.6 Hz, 1H), 4.53 (t, J=5.3 Hz, 1H), 4.82 (t, J=5.3 Hz, 1H), 5.38 (dt, J=6.1, 6.0 Hz, 1H), 7.25 (m, 2H), 7.99 (m, 2H).

To a mixture of Compound 4 (2.94 g) and Compound 14 (2.00 g) in DCM (70 mL) under nitrogen, a mixture of EDC (4.00 g), DMAP (0.73 g) in DCM (5 mL) was slowly added. The mixture was treated as described above for compound 10 to provide Compound 15 (2.31 g): $^1$H NMR (CDCl$_3$, 500 MHz) δ 0.88 (t, J=7.0 Hz, 3H), 1.31 (m, 6H), 1.63 (m, 3H), 1.70 (m, 2H), 1.88 (m, 2H), 2.01 (m, 1H), 2.66 (t, J=7.7 Hz, 2H), 3.62 (dt, J=11.2, 4.8 Hz, 1H), 3.85 (dt, J=10.7, 3.1 Hz, 1H), 3.99 (m, 2H), 4.13 (m, 2H), 4.86 (m, 2H), 5.32 (m, 2H), 5.51 (t, J=3.1 Hz, 1H), 7.08 (m, 2H), 7.25 (m, 2H), 8.00 (m, 2H), 8.03 (m, 2H).

Compound 15 (2.31 g) and pTSA (0.46 g) in THF/MeOH (1:1, 50 mL) was treated as described above for compound 11 to provide Compound 16 (1.79 g): $^1$H NMR (CDCl$_3$, 500 MHz) δ 0.88 (t, J=6.9 Hz, 3H), 1.31 (m, 6H), 1.62 (qui, J=7.5 Hz, 2H), 2.66 (t, J=7.7 Hz, 2H), 4.01 (m, 2H), 4.15 (m, 2H), 4.88 (m, 2H), 5.23 (br s, 1H), 5.33 (m, 2H), 6.85 (m, 2H), 7.25 (m, 2H), 7.98 (m, 2H), 8.00 (m, 2H).

A mixture of Compound 16 (0.50 g), TEA (0.61 mL) in THF (15 mL) was cooled to 0° C. and treated with acryloyl chloride (0.18 mL) in THF (5 mL), as described above for Compound 12, to provide Compound 17 (0.54 g): mp 96-98° C.; $^1$H NMR (CDCl$_3$, 500 MHz) δ 0.88 (t, J=6.9 Hz, 3H), 1.31 (br m, 6H), 1.63 (m, 2H), 2.67 (t, J=7.6 Hz, 2H), 4.00 (m, 2H), 4.14 (dd, J=9.5, 6.4 Hz, 2H), 4.88 (m, 2H), 5.33 (m, 2H), 6.05 (dd, J=10.5, 1.2 Hz, 1H), 6.33 (dd, J=17.3, 10.5 Hz, 1H), 6.64 (dd, J=17.3, 1.1 Hz, 1H), 7.24 (m, 2H), 7.26 (m, 2H), 8.00 (m, 2H), 8.14 (m, 2H).

Example 4

This example illustrates the synthesis of Compound 19 according to Scheme 11:

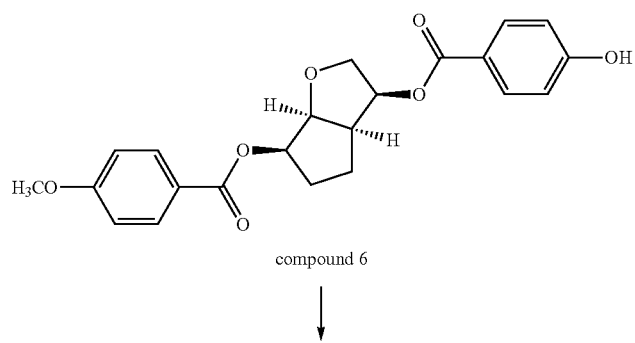

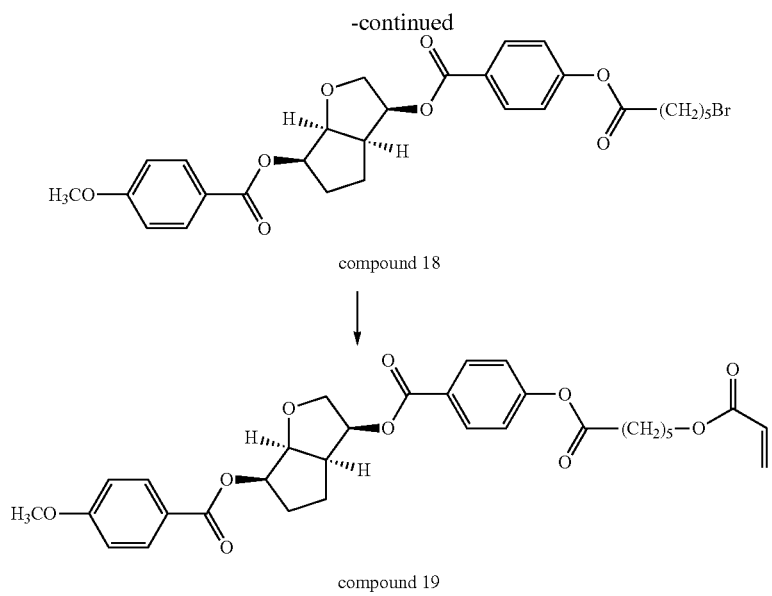

compound 18

↓ compound 19

A mixture of Compound 6 (2.00 g) and TEA (1.53 mL) in THF (15 mL) was cooled to 0° C. A mixture of 6-bromohexanoyl chloride (0.84 mL) in THF (10 mL) was added dropwise. The reaction mixture was allowed to stir at 0° C. for 45 min and at RT for 2.5 h. The reaction mixture was filtered, acidified with dilute HCl, extracted with DCM. The combined organic layer was washed with water, dried, filtered, concentrated, and precipitated in methanol to provide Compound 18 (2.50 g): $^1$H NMR (CDCl$_3$, 500 MHz) δ 1.59 (m, 2H), 1.80 (qui, J=7.6, 2H), 1.94 (qui, J=7.1 Hz, 2H), 2.61 (t, J=7.4 Hz, 2H), 3.44 (t, J=6.7 Hz, 2H), 3.87 (s, 3H), 3.99 (m, 2H), 4.41 (dd, J=9.4, 6.4 Hz, 2H), 4.87 (m, 2H), 5.32 (m, 2H), 6.93 (m, 2H), 7.18 (m, 2H), 8.05 (m, 2H), 8.12 (m, 2H).

To a mixture of Compound 18 (1.00 g), potassium bicarbonate (0.69 g), tetrabutylammonium iodide (TBAI, 0.13 g), 2,6-di-tert-butyl-4-methyl phenol (BHT) (0.03 g), and THF (25 mL), was added acrylic acid (0.18 mL). The mixture was heated to reflux for 4 h. The reaction mixture was added with water, acidified with 0.1 M HCl solution, and extracted with diethyl ether. The combined organic layer was dried, filtered, concentrated. The crude material was purified by silica flash chromatography to provide Compound 19 (0.83 g): mp 49-51° C.; $^1$H NMR (CDCl$_3$, 500 MHz) δ 1.52 (m, 2H), 1.75 (m, 2H), 1.81 (m, 2H), 2.60 (t, J=7.5 Hz, 2H), 3.87 (s, 3H), 3.99 (m, 2H), 4.14 (dd, J=9.4, 6.4 Hz, 2H), 4.20 (t, 6.6 Hz, 2H), 4.87 (m, 2H), 5.32 (m, 2H), 5.82 (dd, J=10.5, 1.5 Hz, 1H), 6.12 (dd, J=17.3, 10.4 Hz, 1H), 6.40 (dd, J=17.4, 1.5 Hz, 1H), 6.93 (m, 2H), 7.18 (m, 2H), 8.05 (m, 2H), 8.12 (m, 2H).

Example 5

This example illustrates the synthesis of Compound 21 according to Scheme 12:

Scheme 12

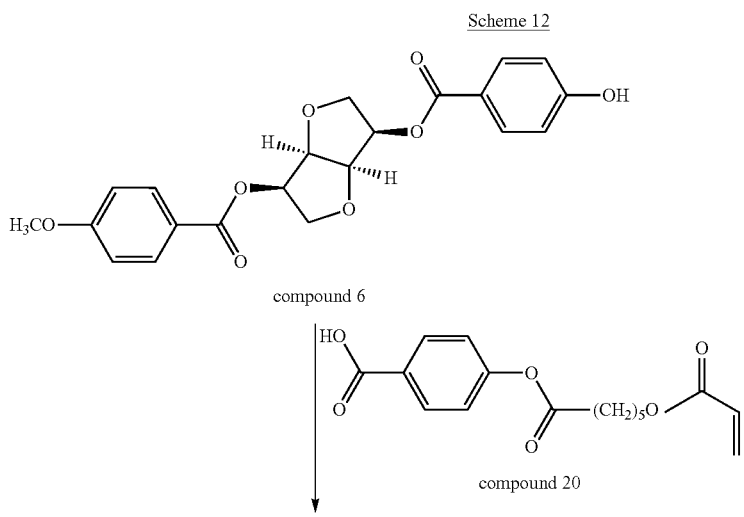

compound 6 compound 20

↓

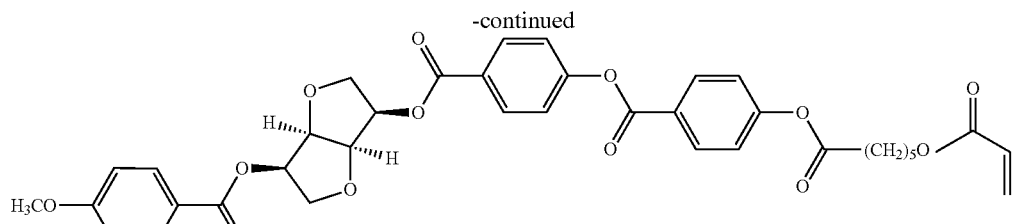

compound 21

First, the synthesis of Compound 20 was preformed following the procedure reported in PCT/JP2005/004389. 6-Hydroxyhexanoic acid was synthesized by base hydrolysis of caprolactone. Caprolactone (100 g) was added to a mixture of potassium hydroxide (145 g), methanol (110 mL), and THF (390 mL). The resulting mixture was stirred at room temperature overnight. The solution was then acidified with HCl and extracted with ethyl acetate. The combined organic layers were washed with water, dried, filtered, and concentrated to obtain 6-hydroxyhexanoic acid. $^1$H NMR (CDCl$_3$, 500 MHz) δ 1.44 (m, 2H), 1.60 (m, 2H), 1.68 (m, 2H), 2.37 (t, J=7.5 Hz, 2H), 3.66 (t, J=6.5 Hz, 2H), 5.80 (br, 1H).

6-Hydroxyhexanoic acid was then converted to 6-acryloyloxyhexanoic acid. A mixture of 6-hydroxyhexanoic acid (10 g), 2,6-di-tert-butyl-4-methylphenol (0.5 g), and DMAc (57 mL) was cooled to 0° C. Acryloyl chloride (17.2 g) was then added dropwise. After stirring for 3.5 hrs, pyridine (12 mL) and water (12 mL) were slowly added. After stirring for another 2 hrs, the solution was acidified with dilute HCl and extracted with ethyl acetate. The combined organic layer was washed with water, dried, filtered, and concentrated to afford 6-acryloyloxyhexanoic acid. $^1$H NMR (CDCl$_3$, 500 MHz) δ 1.46 (m, 2H), 1.70 (m, 4H), 2.37 (t, J=7.3 Hz, 2H), 4.17 (t, J=6.4 Hz, 2H), 5.82 (d, J=10.4 Hz, 1H), 6.12 (dd, J=17.3, 10.5 Hz, 1H), 6.39 (d, J=17.3 Hz, 1H), 11.59 (br, 1H).

Compound 20 was obtained by esterification of 6-acryloyloxyhexanoic acid with 4-hydroxybenzoic acid. A mixture of 6-acryloyloxyhexanoic acid (5.0 g), THF (20 mL), and DMF (5 drops) was cooled to 0° C. Oxalyl chloride (1.70 mL) and THF (25 mL) was then added dropwise. After stirring at 0° C. for 30 min and at RT for 4 hrs, solvent was removed and the resulting acid chloride was re-dissolved in THF (20 mL). To a mixture of 4-hydroxybenzoic acid (2.04 g), TEA (3.74 mL), DMAP (0.16 g) in THF (75 mL) cooled to 0° C., 6-acryloyloxyhexanoic acid chloride in DCM (25 mL) was added dropwise. After stirring at 0° C. for 20 min and at RT for 12 hrs, water was acidified with dilute HCl, extracted with DCM, washed, dried, filtered, and concentrated. The crude mixture was purified by washing with a mixture of isopropanol and hexane to obtain Compound 20 (3.20 g). $^1$H NMR (CDCl$_3$, 500 MHz) δ 1.53 (m, 2H), 1.76 (m, 2H), 1.82 (m, 2H), 2.61 (t, J=7.5 Hz, 2H), 4.20 (t, J=3.2 Hz, 2H), 5.82 (dd, J=10.5, 1.4 Hz, 1H), 6.13 (dd, J=17.3, 10.4 Hz, 1H), 6.41 (dd, J=17.3 Hz, 1.5 Hz, 1H), 7.20 (m, 2H), 8.14 (m, 2H).

A mixture of Compound 20 (0.3 g), THF (15 mL), and DMF (3 drops) was cooled to 0° C. Oxalyl chloride (0.12 mL) in THF (10 mL) was then added dropwise. After stirring at 0° C. for 30 min and at RT for 3.5 h, solvent was removed and the acid chloride was dissolved in DCM (10 mL). To a mixture of Compound 6 (0.37 g), TEA (0.26 mL) and DCM (20 mL) cooled to 0° C., was added dropwise the acid chloride of Compound 20 in DCM (10 mL). After stirring at 0° C. for 30 min and at RT for 4 h, the mixture was acidified with 0.1 M HCl solution, extracted with DCM, washed with water, dried with anhydrous MgSO$_4$, filtered, and concentrated. The crude mixture was purified by washing with a mixture of isopropanol and hexane to obtain Compound 21 (0.22 g): mp 101-102° C.; $^1$H NMR (CDCl$_3$, 500 MHz) δ 1.54 (m, 2H), 1.77 (m, 2H), 1.83 (m, 2H), 2.63 (t, J=7.4 Hz, 2H), 3.87 (s, 3H), 4.01 (m, 2H), 4.15 (dd, J=9.5, 6.3 Hz, 2H), 4.20 (t, J=6.6 Hz, 2H), 4.88 (m, 2H), 5.30-5.38 (br m, 2H), 5.83 (dd, J=10.5, 1.4 Hz, 1H), 6.13 (dd, J=17.3, 10.5 Hz, 1H), 6.41 (dd, J=17.4, 1.4 Hz, 1H), 6.93 (m, 2H), 7.25 (m, 2H), 7.32 (m, 2H), 8.05 (m, 2H), 8.18 (m, 2H), 8.23 (m, 2H).

Example 6

This example illustrates the preparation of Mixture 1 and the preparation of a liquid crystal polymer network.

Mixture 1

Compound 7 (0.037 g), Compound 25 (0.157 g), Compound 26 (0.078 g), Compound 27 (0.059 g), and IRGACURE 184 photoinitiator (Ciba Specialty Chemicals, Ardsley N.Y.) (0.006 g) were combined and dissolved in DCM. The solution was filtered (0.45 micron filter), and the DCM was removed to provide Mixture 1: phase behavior: $1^{st}$ heating: X −30.4 TN* 78.2 I; $1^{st}$ cooling: 170.2 TN* −39.3 X; $2^{nd}$ heating: X −28.5 TN* 80.1 I.

A polyethylene terephthalate film was hand rubbed with a Yoshikawa YA-20-R rubbing cloth (Yoshikawa Chemical Company, Osaka, Japan). Mixture 1 was dissolved in xylenes to provide a 30 wt % solution. The solution was coated by hand using a Wire Size 20 Wire Wound Lab Rod (Paul N. Gardner Company, Pompano Beach, Fla.). The wet coating was heated at 60° C. for 5 min to allow solvent evaporation and alignment of the liquid crystal composition. The coated film was positioned 5.5 cm below a BLAK-RAY long wave UV mercury lamp (Model B-100 AP, UVP Inc., Upland, Calif., with a power of 35 mW/cm$^2$) and was exposed for 5 min under a nitrogen atmosphere to provide a crosslinked polymer network. The crosslinked film exhibited a wavelength of reflection at 711 nm.

Example 7

Mixture 2

Compound 12 (0.030 g), Compound 25 (0.157 g), Compound 26 (0.078 g), Compound 27 (0.059 g), and IRGACURE 184 photoinitiator (0.006 g) were combined and dissolved in DCM. The solution was filtered (0.45 micron filter), and the solvent was removed to provide Mixture 2: phase behavior: $1^{st}$ heating: X −38.4 TN* 80.7 I; $1^{st}$ cooling: 180.3 TN* −33.7; $2^{nd}$ heating: X −31.4 TN* 84.0 I. Coating and polymerization of a film derived from Mixture 2 was performed following similar procedures as described in Example 6 to provide a crosslinked polymer network: wavelength of reflection=830 nm.

Example 8

Mixture 3

Compound 17 (0.030 g), Compound 25 (0.157 g), Compound 26 (0.078 g), Compound 27 (0.059 g), and IRGACURE 184 photoinitiator (0.006 g) were combined and dissolved in DCM. The solution was filtered (0.45 micron filter), and the solvent was removed to provide Mixture 3: phase behavior: $1^{st}$ heating: X −36.4 TN* 63.1 I; $1^{st}$ cooling: 178.3 TN* −32.6; $2^{nd}$ heating: X −31.9 TN* 82.8 I. Coating and polymerization of a film derived from Mixture 2 was performed following similar procedures as described in Example 6 to provide a crosslinked polymer network: wavelength of reflection=981 nm.

Example 9

Mixture 4

Compound 19 (0.037 g), Compound 25 (0.157 g), Compound 26 (0.078 g), Compound 27 (0.059 g), and IRGACURE 184 photoinitiator (0.006 g) were combined and dissolved in DCM. The solution was filtered (0.45 micron filter), and the solvent was removed to provide Mixture 4: phase behavior: $1^{st}$ heating: X −35.9 TN* 81.8 I; $1^{st}$ cooling: 181.5 TN* −33.7; $2^{nd}$ heating: X −30.9 TN* 85.9 I. The crosslinked polymer network of Mixture 4 was prepared following similar procedures as described in Example 6: wavelength of reflection=785 nm.

Example 10

Mixture 5

Compound 21 (0.037 g), Compound 25 (0.157 g), Compound 26 (0.078 g), Compound 27 (0.059 g), and IRGACURE 184 photoinitiator (0.006 g) were combined and dissolved in DCM. The solution was filtered (0.45 micron filter), and the DCM was removed to provide Mixture 5: phase behavior: $1^{st}$ heating: X −34.6 TN* 71.4 I; $1^{st}$ cooling: 186.7 TN* −31.9; $2^{nd}$ heating: X −29.2 TN* 91.5 I.

The crosslinked polymer network of Mixture 5 was prepared following similar procedures as described in Example 6: wavelength of reflection=717 nm.

Comparative Example A

A Comparative Example A, similar to that disclosed in WO 2006/128091, illustrates the formation of a polymer network based upon a twisted nematic layer induced by an isosorbide containing ester. A blend of Compound 26 (22.7 parts), Compound 25 (53.4 parts), Compound 27 (15 parts), Compound D (the isosorbide ester shown below, 6.9 parts) and IRGACURE 184 photoinitiator was prepared and coated as a 33.3 w/v % solution in xylenes and cured in a similar manner as Example 6.

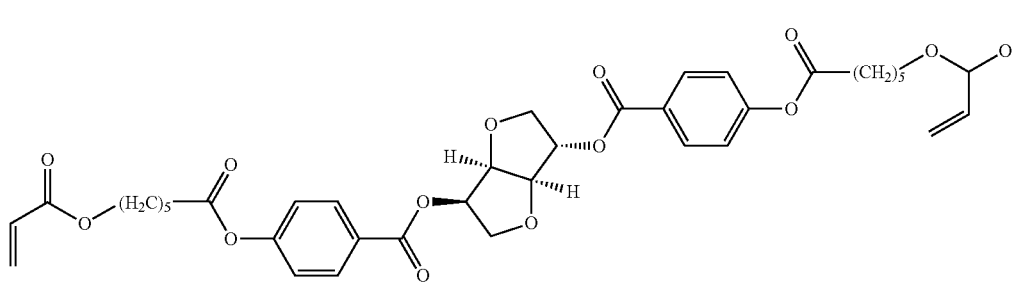

Compound D

Example 11

The handedness of reflected circularly polarized light was determined by examining cured films of Example 7 and that of Comparative example A, according to well known procedures described in W. A. Shurcliff, "Polarized Light: Production and Use", Harvard University Press, (1962). According to this procedure a quarter wave-plate was positioned in between the sample film to be tested and a linear polarizer. The quarter wave-plate was oriented with the slow axis at −45 degrees relative to the electric field of the linear polarizer. If reflected light from the sample transmitted through the linear polarizer, this was an indication that the reflected light was right-hand circularly polarized (RHCPL). Conversely, when the quarter wave-plate was oriented with the slow axis at +45 degrees relative to the electric field of the linear polarizer, the observation that the reflected light from the sample transmitted through the linear polarizer indicated that the reflected light was LHCPL. The polymer network provided by Comparative Example A, that incorporated a chiral dopant based on the isosorbide moiety, reflected RHCPL. Example 7 which incorporated a chiral dopant based on the isomannide moiety reflected LHCPL.

Example 12

Mixture 7

Compound 7 (0.15 g), Compound 25 (0.415 g), Compound 26 (0.415 g), and Irgacure 184 (0.02 g) were combined and dissolved in DCM. The solution was filtered (0.45 micron filter), and the DCM was removed to provide Mixture 7. Mixture 7 was dissolved in xylenes to provide a 30 wt % solution. The solution was coated and cured at RT following similar procedures as described in Example 6 to provide a crosslinked polymer network 12A: wavelength of reflection=499 nm.

In another cure run, Mixture 7 solution was coated and dried as described in Example 6, and the sample was purged with a nitrogen atmosphere at 60° C. and cured at 60° C. to provide a crosslinked polymer network 12B: wavelength of reflection at 464 nm. The 12B sample cured at 60° C. exhibited less haze than the 12A sample cured at RT.

Each of the formulae shown herein describes each and all of the separate, individual compounds that can be assembled in that formula by (1) selection from within the prescribed range for one of the variable radicals, substituents or numerical coefficents while all of the other variable radicals, substituents or numerical coefficents are held constant, and (2) performing in turn the same selection from within the prescribed range for each of the other variable radicals, substituents or numerical coefficents with the others being held constant. In addition to a selection made within the prescribed range for any of the variable radicals, substituents or numerical coefficents of only one of the members of the group described by the range, a plurality of compounds may be described by selecting more than one but less than all of the members of the whole group of radicals, substituents or numerical coefficents. When the selection made within the prescribed range for any of the variable radicals, substituents or numerical coefficents is a subgroup containing (i) only one of the members of the whole group described by the range, or (ii) more than one but less than all of the members of the whole group, the selected member(s) are selected by omitting those member(s) of the whole group that are not selected to form the subgroup. The compound, or plurality of compounds, may in such event be characterized by a definition of one or more of the variable radicals, substituents or numerical coefficents that refers to the whole group of the prescribed range for that variable but where the member(s) omitted to form the subgroup are absent from the whole group.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the subject matter hereof, however, may be stated or described as consisting essentially of certain features or elements, in which embodiment features or elements that would materially alter the principle of operation or the distinguishing characteristics of the embodiment are not present therein. A further alternative embodiment of the subject matter hereof may be stated or described as consisting of certain features or elements, in which embodiment, or in insubstantial variations thereof, only the features or elements specifically stated or described are present.

All patents and patent publications cited herein are hereby incorporated as a part hereof by reference.

What is claimed is:

1. A compound as represented by the structure of formula (I):

$$R(S_5A_1)_r(S_3B_1)_pS_1\text{-}D\text{-}S_2(B_2S_4)_q(A_2S_6)_tR_p \qquad (I)$$

wherein

D is the divalent moiety:

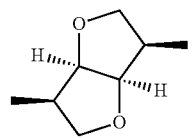

$S_1$ and $S_2$ are linking groups each independently selected from the group consisting of —O—, —OC(O)—, and —OC(O)O—;

$S_3$, $S_4$, $S_5$, and $S_6$, are linking groups each independently selected from the group consisting of covalent bond, —O—, —S—, —C(O)—, —OC(O)—, —C(O)O—, —OC(O)O—, —OC(O)NR$_1$—, —NR$_1$C(O)O—, —SC(O)—, and —C(O)S—;

$R_1$ is hydrogen or $C_1$ to $C_4$ alkyl;

each $B_1$ and $B_2$ is a divalent radical independently selected from the group consisting of aliphatic and aromatic carbocyclic and heterocyclic groups having 1 to 16 carbon atoms; optionally having one or more fused rings and optionally mono- or polysubstituted with L;

L is selected from the group consisting of the substituents F, Cl, —CN, and —NO$_2$; and alkyl, alkoxy, alkylcarbonyl, and alkoxycarbonyl groups, having 1 to 8 carbon atoms, wherein one or more of the carbon atoms are optionally substituted with F or Cl;

$A_1$ is a divalent linear or branched alkyl having 2 to 20 carbon atoms, optionally interrupted by linking groups selected from the group —O—, —S—, —C(O)—, —OC(O)— and —C(O)O—;

$A_2$ is a divalent linear or branched alkyl having 3 to 20 carbon atoms, optionally interrupted by linking groups selected from the group —O—, —S—, —C(O)—, —OC(O)— and —C(O)O—;

R is selected from the group consisting of hydrogen, F, Cl, —CN, —NO$_2$, and a monovalent linear or branched alkyl having 1 to 20 carbon atoms, optionally interrupted by linking groups selected from the group —O—, —S—, —C(O)—, —OC(O)— or —C(O)O—;

$R_p$ is a polymerizable group;

p and q are each independently an integer of 1 or 2; and r and t are each independently an integer of 0 or 1;

provided that when R is hydrogen, F, Cl, —CN, or —NO$_2$, and r is 1, $S_5$ is a covalent bond; and when R is hydrogen, F, Cl, —CN, or —NO$_2$, and r is 0, $S_3$ is a covalent bond.

2. The compound of claim 1 wherein —R$_p$ is selected from the group consisting of CH$_2$=C(R$_2$)—, glycidyl ether, propenyl ether, oxetane, and 1,2-, 1,3-, and 1,4-substituted styryl and alkyl substituted styryl radicals, wherein R$_2$ is hydrogen, Cl, F, or CH$_3$.

3. The compound of claim 1 wherein t=0, the radical —S$_4$—R$_p$ is CH$_2$=C(R$_2$)—C(O)—O—, and R$_2$ is hydrogen or —CH$_3$.

4. The compound of claim 1 wherein t=1 and the radical —S$_6$—R$_p$ is CH$_2$=C(R$_2$)—C(O)—O—, and R$_2$ is hydrogen or —CH$_3$.

5. The compound of claim 1 wherein $S_1$ and $S_2$ are —OC(O)—.

6. The compound of claim 1 wherein $B_1$ and $B_2$ are each independently divalent radicals selected from the group consisting of 1,4-cyclohexyl; 2,6-naphthyl; 4,4'-biphenyl; and R$_{11}$-substituted-1,4-phenyl, wherein R$_{11}$ is H, —CH$_3$ or —OCH$_3$.

7. The compound of claim 1 wherein formula (I) is formula (II):

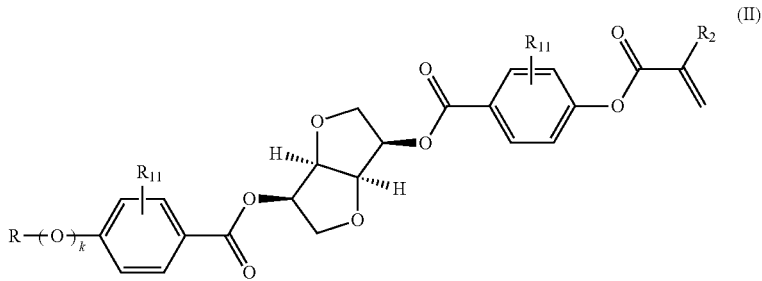

wherein k is 0 or 1; R is a linear or branched $C_1$-$C_{20}$ alkyl; $R_{11}$ is H, —$CH_3$ or —$OCH_3$; and $R_2$ is hydrogen, Cl, F, or $CH_3$.

8. The compound of claim 1 wherein formula (I) is formula (III):

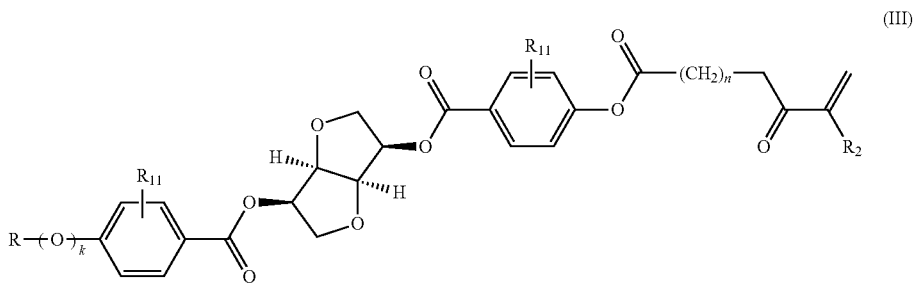

wherein k is 0 or 1; n is an integer of 3 to 20; R is a linear or branched $C_1$-$C_{20}$ alkyl; $R_{11}$ is H, —$CH_3$ or —$OCH_3$; and $R_2$ is hydrogen, Cl, F, or $CH_3$.

9. The compound of claim 1 wherein formula (I) is formula (IV):

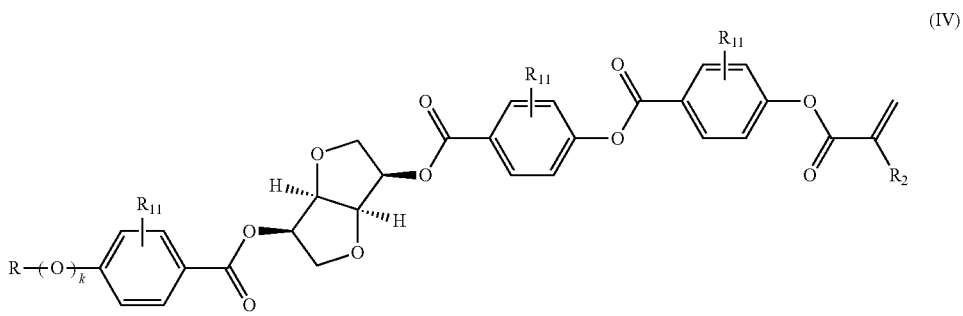

wherein k is 0 or 1; R is a linear or branched $C_1$-$C_{20}$ alkyl; $R_{11}$ is H, —$CH_3$ or —$OCH_3$; and $R_2$ is hydrogen, Cl, F, or $CH_3$.

10. The compound of claim 1 wherein formula (I) is formula (V):

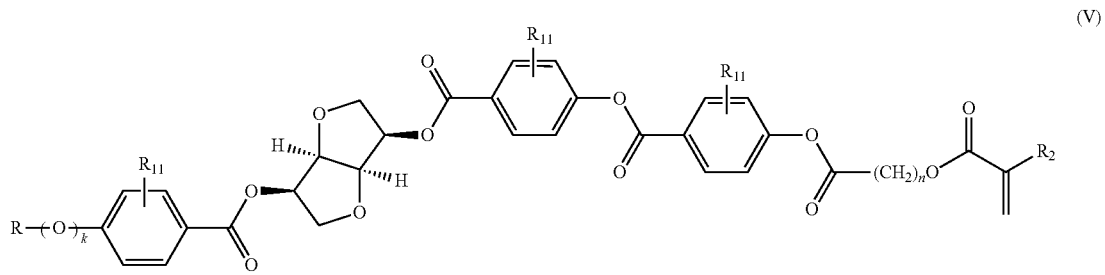

(V)

wherein k is 0 or 1; n is an integer of 3 to 20; R is a linear or branched $C_1$-$C_{20}$ alkyl; $R_{11}$ is H, —$CH_3$ or —$OCH_3$; and $R_2$ is hydrogen, Cl, F, or $CH_3$.

11. The compound of claim 1 wherein formula (I) is formula (VI):

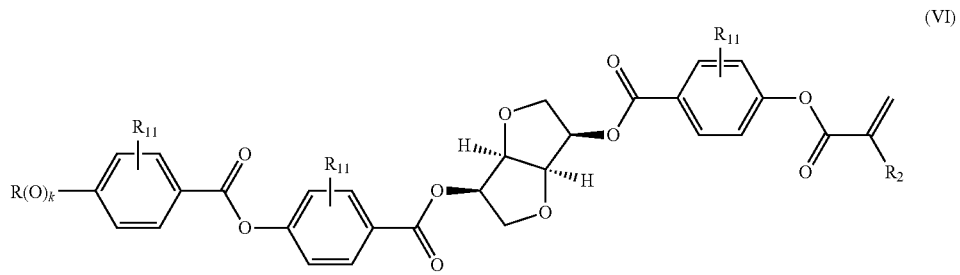

(VI)

wherein k is 0 or 1, R is a linear or branched $C_1$-$C_{20}$ alkyl; $R_{11}$ is H, —$CH_3$ or —$OCH_3$; and $R_2$ is hydrogen, Cl, F, or $CH_3$.

12. A polymerizable liquid crystal composition comprising at least one compound of claim 1.

13. The polymerizable liquid crystal composition of claim 12 further comprising a compound of formula (VII):

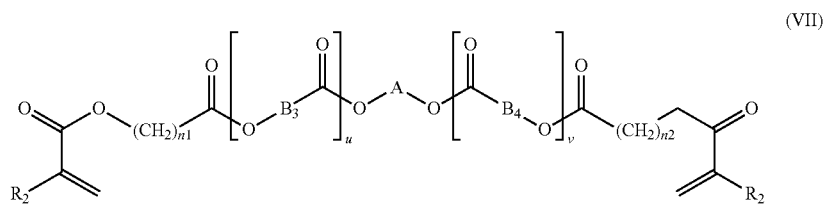

(VII)

wherein
 $R_2$ is independently selected from the group: H, F, Cl, and $CH_3$;
 n1 and n2 are, independently, integers 3 to 20;
 u and v are, independently, integers 0, 1 or 2;
 A is a divalent radical selected from the group:

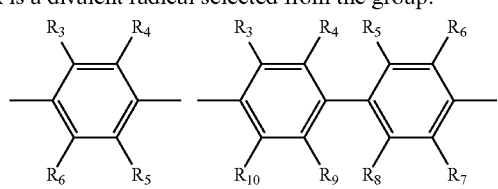

-continued

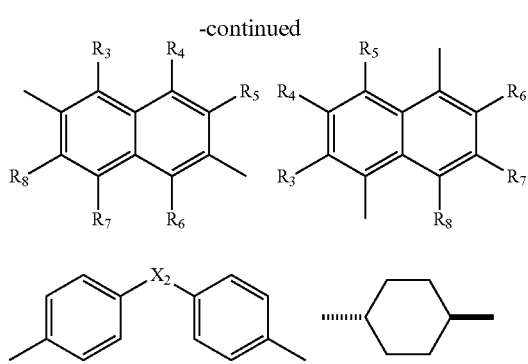

wherein
- $R_3$-$R_{10}$ are independently selected from the group: H, $C_1$-$C_8$ straight or branched chain alkyl, $C_1$-$C_8$ straight or branched chain alkyloxy, F, Cl, phenyl, —C(O)CH$_3$, CN, and CF$_3$;
- $X_2$ is a divalent radical selected from the group: —O—, —(CH$_3$)$_2$C—, and —(CF$_3$)$_2$C—; and
- each $B_3$ and $B_4$ is a divalent radical independently selected from the group: 2,6-naphthyl; 4,4'-biphenyl; and $R_{11}$-substituted-1,4-phenyl, wherein $R_{11}$ is H, —CH$_3$ or —OCH$_3$;

with the proviso that when the sum of u+v is equal to 3 or 4, at least two of $B_3$ and $B_4$ are $R_{11}$-substituted-1,4-phenyl.

14. The polymerizable liquid crystal composition of claim 12 wherein, within formula (VII), u is 1 and v is 0, and formula (VII) is formula (VIIIa):

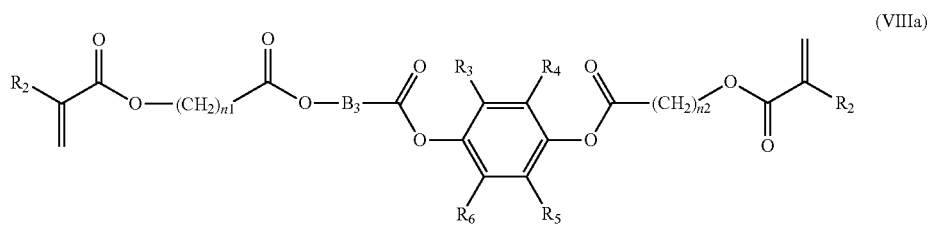

(VIIIa)

wherein $R_2$ is independently H or CH$_3$; $R_3$-$R_6$ are independently H or —CH$_3$; and $B_3$ is $R_{11}$-substituted-1,4-phenyl, wherein $R_{11}$ is H, —CH$_3$ or —OCH$_3$.

15. The polymerizable liquid crystal composition of claim 12 wherein, within formula (VII), u and v are 1, and formula (VII) is formula (IXa):

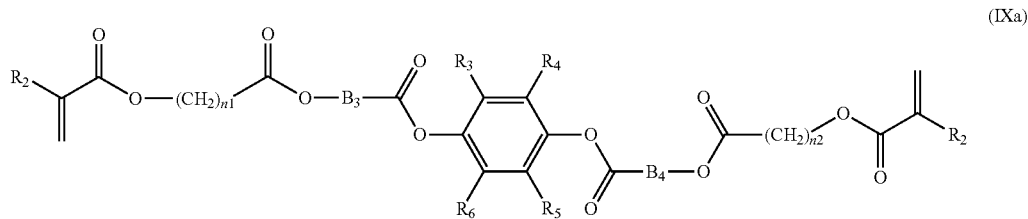

(IXa)

wherein $R_2$ is independently H or CH$_3$; $R_3$-$R_6$ are independently H or —CH$_3$; and $B_3$ and $B_4$ are $R_{11}$-substituted-1,4-phenyl, wherein $R_{11}$ is H, —CH$_3$ or —OCH$_3$.

16. A polymer network derived from polymerization of the composition of claim 12 or 13.

17. The polymer network of claim 16 that reflects left-hand circularly polarized light.

18. The polymer network of claim 17 having a wavelength of maximum reflection in the range of about 280 to about 2000 nm.

19. The polymer network of claim 17 having a wavelength of maximum reflection in the range of 700 to about 1200 nm.

20. The polymer network of claim 16 that is an optical element.

* * * * *